(12) United States Patent
Beavers

(10) Patent No.: US 8,003,136 B2
(45) Date of Patent: *Aug. 23, 2011

(54) STANDARDIZATION OF BOTANICAL PRODUCTS UTILIZING BIOLOGICAL ACTIVITY AS A MARKER

(76) Inventor: Randy Beavers, Dalton, GA (US)

( * ) Notice: Subject to any disclaimer, the term of this patent is extended or adjusted under 35 U.S.C. 154(b) by 638 days.

This patent is subject to a terminal disclaimer.

(21) Appl. No.: 11/882,270

(22) Filed: Jul. 31, 2007

(65) Prior Publication Data

US 2008/0038196 A1  Feb. 14, 2008

Related U.S. Application Data

(63) Continuation-in-part of application No. 11/070,891, filed on Mar. 3, 2005.

(60) Provisional application No. 60/549,747, filed on Mar. 3, 2004.

(51) Int. Cl.
*A61K 36/00* (2006.01)
*A61K 49/00* (2006.01)

(52) U.S. Cl. .......................................... 424/725; 424/9.1
(58) Field of Classification Search ........................ None
See application file for complete search history.

*Primary Examiner* — Christopher R Tate
*Assistant Examiner* — Randall Winston
(74) *Attorney, Agent, or Firm* — Bio Intellectual Property Services LLC Bio IPS; O. (Sam) Zaghmout

(57) ABSTRACT

The present invention relates generally to herbal materials and methods for making such materials in medicinally useful and pharmaceutically acceptable forms. Particularly, the present invention relates generally to *Hydrastis canadensis* (goldenseal) materials and methods for making such materials in medicinally useful and pharmaceutically acceptable forms. More particularly, the present invention relates a process which allows the standardization of the product to specified levels of bioactivity in both hydro-alcoholic tinctures and solid extracts in the processing of goldenseal materials to produce extracts which qualify as pharmaceutical grade compositions which are suitable for use in clinical or veterinary settings to treat and/or ameliorate diseases, disorders or conditions.

5 Claims, 8 Drawing Sheets

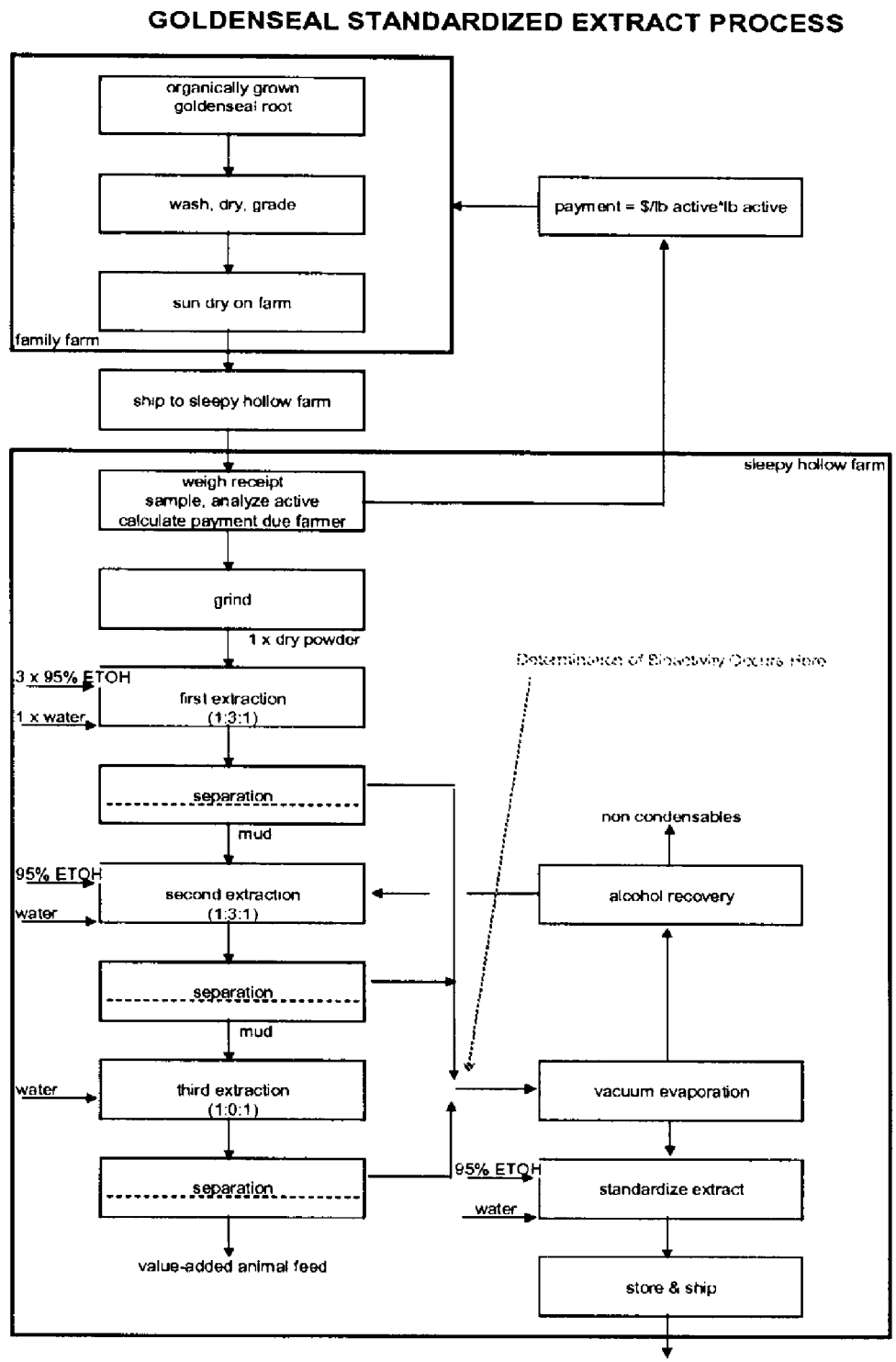
FIG. 1. Diagram of Production Process

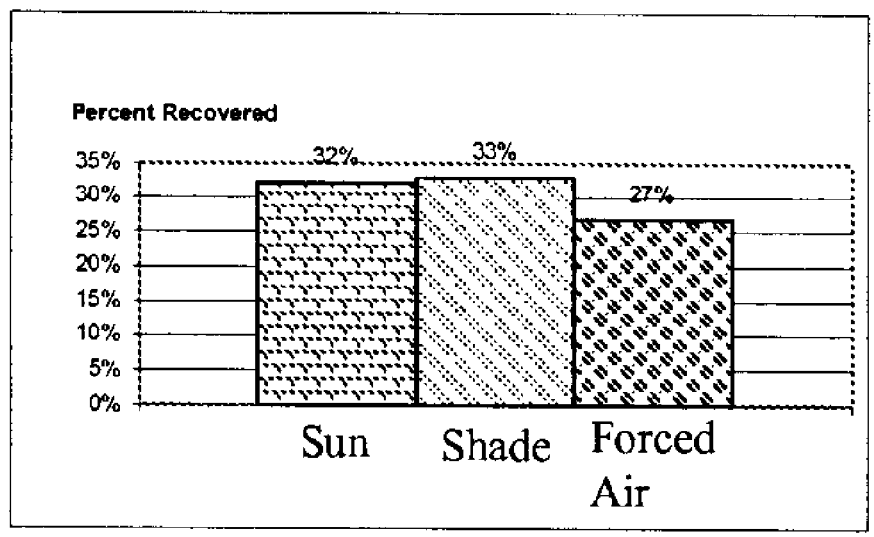
FIG.2. Relative Recoveries from three Methods of Drying One Pound of Fresh Goldenseal.

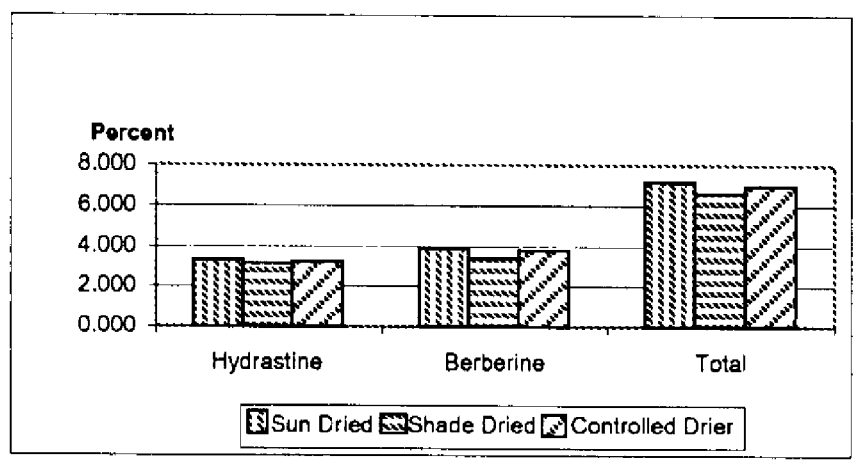
FIG.3. Hydrastine/Berberine Content of Goldenseal after Three Methods of Drying

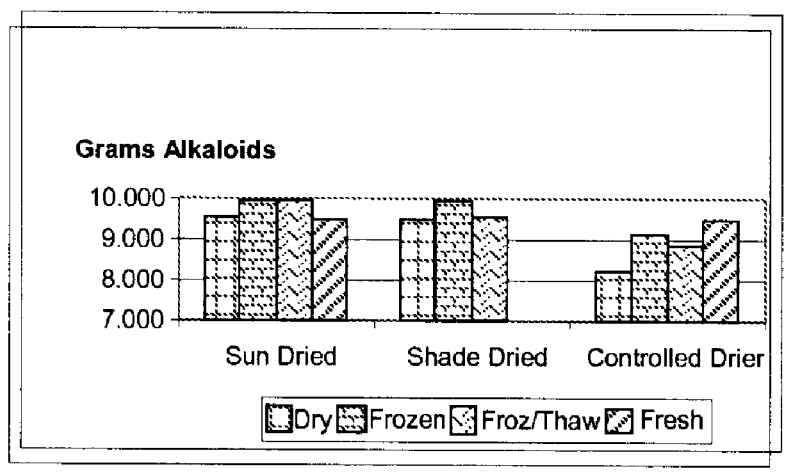
FIG.4. Net effect of drying and grinding goldenseal on gross alkaloids avialable for extraction compared with fresh Material.

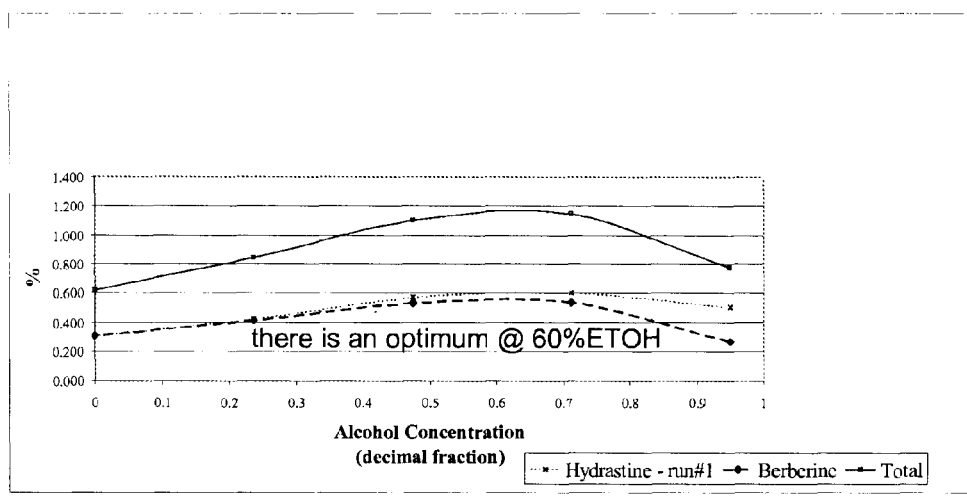
FIG.5. Alkaloid Extraction as a function of Alcohol Concentration.

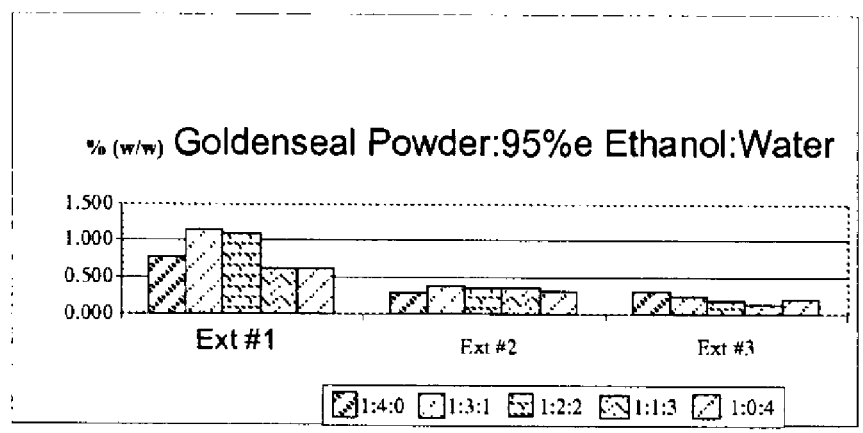
FIG.6. Combined hydrastine/berberine recovered from five different solvent levels over three extractions

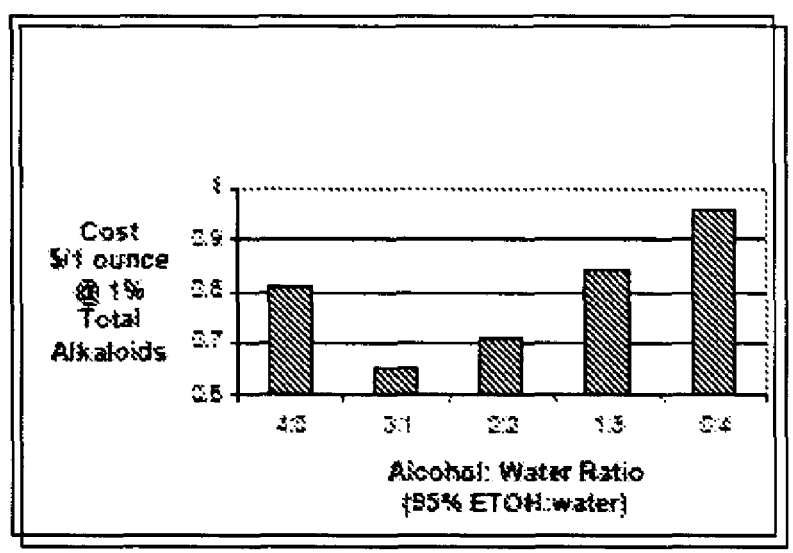
FIG.7. Goldenseal Extraction Cost Optimization

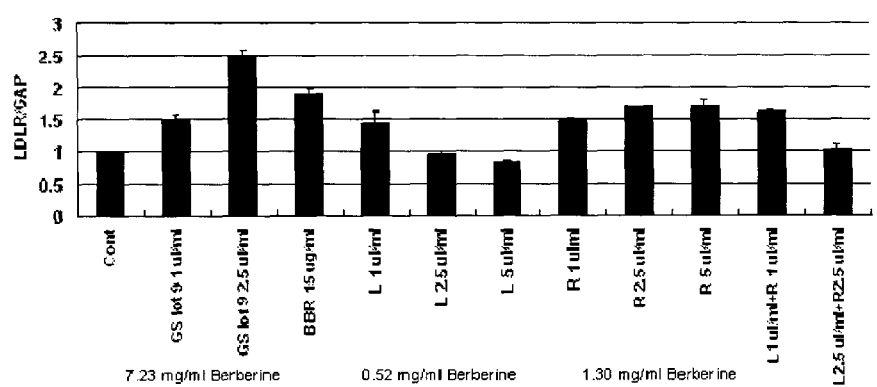
Fig. 8. Effect of sleep Hollow Farm GS on LDLR message in Hep G2 after 16 hrs

STANDARDIZATION OF BOTANICAL PRODUCTS UTILIZING BIOLOGICAL ACTIVITY AS A MARKER

CROSS REFERENCE TO RELATED APPLICATIONS

This application is a continuation-in-part of application Ser. No. 11/070,891, filed Mar. 3, 2005, which claims the benefit of U.S. Provisional Application No. 60/549,747, filed Mar. 3, 2004. The entire disclosure of the prior applications is hereby incorporated by reference.

STATEMENT AS TO RIGHTS TO INVENTIONS MADE UNDER FEDERALLY SPONSORED RESEARCH OR DEVELOPMENT

This invention was made with United States Government support under Grant Nos. 2003-33610-13119 and USDA Grant # 204-33610-14721 Phase II SBIR, awarded by United States Department of Agriculture. The United States Government has certain rights in this invention.

SEQUENCE LISTING OR PROGRAM

Not Applicable

FIELD OF THE INVENTION

The lack of standard levels of pharmacologically active compounds in natural botanical products has resulted in a reluctance by health care providers to prescribe these products for their patients. This problem is compounded by the fact that even when botanical products are standardized to specific levels of a marker compound, variations in the content of other oftentimes unknown compounds caused by a wide range of factors such as soil temperature and pH, air temperature, rainfall, and genetics, results in unpredictable biological activity. Additionally, raw material integrity is vital to the production of a safe and effective product. Therefore, this invention is directed to a method of assuring reproducibility of an extraction process. The present invention is also directed to a method of reproducibly extracting a pharmacologically active mixture of chemical components from a biological source, particularly a plant source. Furthermore, the present invention is directed to a method of manipulating the pharmacologically active compound concentration levels within said pharmacologically active mixture of chemical compounds relative to certain other unknown compounds within the mixture. Thus, the method delivers a pharmaceutical grade product with a desired level of bioactivity without adulteration of any kind. The present invention also reveals a composition of botanical material with enhanced biological activity when compared with the individual parts or the sum of the parts.

BACKGROUND OF THE INVENTION

Plants have been, and continue to be, the primary source of a wide variety of medicinal compounds. For centuries, various forms of botanically derived materials have been used to treat countless different ailments. The botanical materials have typically been in the form of powders made from one or more plants or plant parts or extracts derived from whole plants or selected plant parts. These powders and extracts are, for the most part, complex mixtures of both biologically active and biologically inactive compounds.

In modern day, herbal medicine, although gaining some acceptance in Western society, still faces several specific challenges. First, in the opinion of many highly trained medical practitioners, there is the view that herbal medicine lacks sufficient scientific support data in our highly technical and science oriented society. Secondly, there is concern about which components of an herbal remedy are pharmaceutically effective. Furthermore, the question arises as to the concentrations or dosages present of such pharmaceutically effective components of herbal remedies. In short, traditional medical practitioners are concerned with a lack of both qualitative and quantitative standards for herbal medications. Such a lack of standardization is viewed as hindering the ability to prescribe and adjust dosages of such nontraditional or herbal medications. The lack of such standardization has also lead to a reluctance on the part of regulatory agencies in funding further investigation and acceptance of such nontraditional medications.

Although not meeting some of the criteria of Western traditional medicine, such herbal compositions are known to be quite effective in treatment of a variety of maladies with little or no side effects. In part, the pharmaceutical activity in many instances is attributable not only to the presence of specific biologically active compounds but also to a synergistic effect resulting from the combination of two or more chemical components present in the herbal mixture.

Since herbal treatments, defined as both herbal medications and biologically enhancing herbal compositions, are derived from plants, the chemical composition of such herbal treatments varies according to a number of factors, not the least of which are the genetic composition and growing conditions in which the plant is produced as well as the harvest conditions and isolation of the active components of the plant.

Accordingly, biological variants of a particular plant may typically be expected to produce significant variations in quantities of particular chemical components found in the plant. Likewise, even in the same biological variant of a plant, differences in soil, moisture and other growing conditions may significantly affect the quantities of specific chemical components produced by the plant.

The vast majority of the raw material used to produce botanical products is currently collected form the wild. Wild collected plants are, by definition, produced outside of a controlled environment. This has presented a unique problem for manufacturers of botanical products desiring the control, reproducibility, and standardization that are required of pharmaceuticals. This problem is due primarily to the plurality of components contained in an herbal medicine and the large variation in composition and potency due to the growing, harvesting and processing conditions. Therefore it is desirable to standardize these growing conditions to the extent possible.

Finally, the manner in which a plant is processed can drastically influence the relative proportions and total amounts of specific chemical components isolated from the plant. Thus, such steps as harvesting, storage, reduction in particle size, expression of liquid components and extraction all determine the proportions and amounts of chemical components and hence the pharmaceutical activity of the isolated product.

Considering the many factors which influence the composition and pharmaceutical activity of herbal compositions, it is desirable to employ methods which result in the standardization of herbal compositions both with respect to the chemical compositions thereof and the pharmaceutical activity of such chemical mixtures. In addition, it is desirable to standardize the processing conditions in order to obtain such standardized herbal compositions. Furthermore, being able to accurately determine and compare the compositions of biological mixtures, particularly plant or herbal mixtures, would allow processing conditions to be controlled to obtain reliable pharmacological activity. With such methods available to the scientific community, not only would physicians be able to prescribe specified dosages of herbal compositions with confidence, but herbal composition "manufacturers" would achieve predictable pharmaceutical activity of such mixtures, improved quality control and the ability to differentiate herbal mixtures from varying sources.

Pharmaceutical grade botanical products are advantageous in that they allow careful tracking of the effects of individual compounds, in treatment protocols. Further, the dosage of the drug can be carefully controlled to provide relatively predictable medicinal action. The potential benefit provided by the use of herbal product as medicine is believed by many industry experts to be outweighed by the clinical risks associated with the absence of standard levels of biologically active materials from natural plants. In that respect, herbal products are not well characterized or controlled in a clinical setting.

The present invention is a significant advancement in the field of making herbal extracts for medicinal purposes, providing precise levels of both berberine and hydrastine while at the same time maintaining USDA National Organic Program (NOP) organic certification. The invention offers tremendous benefits since the extract is standardized to biological activity rather than just a chemical marker. This allows for the use of exact quantities of the extract necessary to produce the desired pharmacological activity instead of potentially toxic high doses or ineffective low doses produced by current methods. The invention also permits the manipulation and/or removal of certain pharmacologically active compounds from the extract thereby allowing more precise calculation of the contribution of each compound's activity to that of the whole and permits various ratios of the compounds in the final product based on the results of certain bioassays. In addition, pre-standardization by cultivation and harvesting practices results in higher concentrations of pharmacologically active compounds in the raw material which translates into reduced processing to produce a given amount of extract. Maintenance of USDA NOP certification throughout the production process provides third party certification that the product has been produced in a sustainable manner, important due to many medicinal plant's endangered status, and that no potentially toxic materials such as herbicides, pesticides, or artificial fertilizers have been used.

In one object of this invention, a method was developed for standardizing the levels of biologically active materials from natural plants including, but not limited to, herbal plants. In a more preferable object of this invention, the method is suitable for producing pharmaceutical grade natural products standardized to a specific level of bio-activity from *Hydrastis canadensis* Linn. (goldenseal) and other berberine and/or hydrastine containing plants. In a preferable object of this invention, the method disclosed is suitable for the precise standardization of marker compounds generally recognized as indicators for the quality of goldenseal. In a more preferable object of this invention, the marker compounds are berberine and hydrastine.

Background Information Regarding Goldenseal

Goldenseal belongs to the Family Ranunculaceae and is a small hairy perennial which in a natural environment generally emerges in early spring (mid-March to early May) and dies down in mid-August to late-September. The root system is composed of a bright yellow horizontal rhizome, 2 to ¾ inch thick, marked by cup-like depressions where the annual stem falls away. Mature plants (at least 3 years old) are 6-14 inches tall and have two or more hairy stems usually ending in a fork with two leaves. The 5-7 lobed, palmate, double-toothed leaves are 3-12 inches wide and 3-8 inches long. After emergence in early spring, flower buds quickly develop and small inconspicuous white flowers open as the leaves unfold. Plants started from seed usually flower the third or fourth year. Each plant can produce a single, green raspberry like fruit which turns red and ripens in July (Davis, 2000).

Goldenseal is one of the most popular medicinal herbs in the US and has been wild collected from the forests of Eastern North America for hundreds of years. Its historical range extended from Vermont to Georgia to Arkansas to Minnesota (Foster, 1990). Goldenseal's popularity has resulted in it being overcollected from the wild. Goldenseal is listed as an Endangered Species in Georgia, North Carolina, Vermont, Connecticut, Massachusetts, and Minnesota. The USFWS has stated that goldenseal is either endangered, threatened, imperiled, rare, or uncommon in all 27 U.S. states which have native populations (USFWS, 1997). The US government, in 1997, backed a proposal to place Goldenseal on the Convention on International Trade in Endangered Species (CITES) Appendix List II, which was approved. The CITES listing requires the goldenseal produced for export be cultivated for minimum of four years. The present invention addresses this problem through the development of a "wild simulated" production system for goldenseal.

The alkaloids berberine and hydrastine are commonly used by industry as markers to indicate the quality of raw goldenseal although the most common level of consumer product assurance is that of a specified percentage of total alkaloid content, unspecified as which alkaloid or how much of each. These two compounds are also thought to be the primary bio-active compounds in the plant. (Abourashed, 2001, Govindan, 1999) Proposed United States Pharmacopoeia (USP) standards for dried goldenseal root and rhizome are not less than 2.0% hydrastine and not less than 2.5% berberine.

The alkaloid content variability of both raw goldenseal and consumer products currently on the market was clearly demonstrated in Govindan (1999), where ten samples (eight— raw powdered material, GS-1 through GS-8 and two—powdered material from off-the-shelf capsules, GS-9 and GS-10) were analyzed using Thin-Layer Chromatography (TLC). Five of the samples contained both berberine and hydrastine, four contained only berberine, and one contained neither. These results were verified by High Pressure Liquid Chromatography (HPLC)(Govindan, 1999). Hydrastine is unique to goldenseal among North American plants therefore the absence of hydrastine is a strong indication that the material purported to be goldenseal root and rhizome is probably not goldenseal at all. Extremely low quantities of hydrastine are also indicative of adulteration with other berberine containing plants such as various *Berberis* species. Discovery of palmatine in purported goldenseal material, common in other berberine producing plants but absent in goldenseal, is a definitive indication of adulteration (Weber, 2003). In addition only three of the ten samples tested approximated the profile of the raw goldenseal used by the National Toxicological Program for their studies (MRI, 2001). Our 2003 harvest Sleepy Hollow Farm-1 (SHF-1) had the second highest combined hydrastine/berberine total of all the samples listed. See table 1 below.

The present invention provides both a method of standardized processing procedures and of obtaining biological compositions having a desired level of pharmaceutical activity from plants containing berberine and/or hydrastine, preferably goldenseal. The present invention also permits the isolation of biological compositions or components, and in particular herbal compositions or components, having high, or the highest pharmacological activity obtainable by a specific process, such as extraction.

TABLE 1

Results of TLC and HPLC analysis of 10 goldenseal samples (GS-1-GS-10)[a], National Toxicological Program Sample(NTP-1)[b], one commercial product analyzed in Weber, et al, (1999)[c] and Sleepy Hollow Farms 2003 harvest.

| Sample | Hydrastine | | Berberine | | Hydrastinine | |
|---|---|---|---|---|---|---|
| | TLC | HPLC(%) | TLC | HPLC(%) | TLC | HPLC(%) |
| GS-1 | +++ | n.a. | +++ | n.a | + | n.a. |
| GS-2 | +++ | 2.68 | +++ | 4.27 | + | n.a. |
| GS-3 | − | − | ++ | 0.56 | + | n.a. |
| GS-4 | +++ | 2.34 | +++ | 3.48 | + | n.a. |
| GS-5 | +++ | 3.22 | +++ | 4.54 | + | n.a. |
| GS-6 | + | 0.60 | ++ | 0.56 | − | n.a. |
| GS-7 | − | − | ++ | 0.28 | − | n.a. |
| GS-8 | − | − | − | − | − | n.a. |
| GS-9 | − | − | +++ | 1.51 | − | n.a |
| GS-10 | − | − | +++ | 5.31 | − | n.a. |
| NTP-1 | n.a. | 3.02 | n.a. | 3.45 | n.a. | n.a. |
| Weber-1 | n.a. | 1.30 | n.a. | 1.90 | n.a. | n.a. |
| SHF-1 | n.a. | 3.31 | n.a. | 3.96 | n.a. | n.a. |

[a]Relative amounts based on the visual estimation of the size and intensity of spots on TLC: dark spot(+++); medium intensity spot(++); low intensity spot(+); not visible(−); not analyzed(n.a.)(Govindan, 1999).
[b](MRI, 2001)
[c](Weber, et al., 1999)

Uses of Goldenseal and/or its Isolated Alkaloids Berberine/Hydrastine

Goldenseal was first used by Native Americans to treat wounds, ulcers, digestive disorders, and skin and eye ailments. Over the years goldenseal has been used to treat a variety of digestive and hemorrhagic disorders. It is thought to possess antiseptic, astringent, and hemostatic qualities when applied topically. It is thought by some that goldenseal is effective in the treatment of diarrhea, hemorrhoids, disorders of the genito-urinary tract, upper respiratory inflammation and congestion, mucous membrane inflammation, eczema, pruritus, otorrhea, tinnitus and congestion/inflammation of the ear, and conjunctivitis, as well as for cancers, particularly of the ovary, uterus, and stomach. Goldenseal has been used as a tonic, antiperiodic, diuretic, and as a vaginal douche. It is commonly consumed in capsules, liquid herbal extracts, and as an herbal tea.

Although at least 10 isoquinoline alkaloids have been identified in goldenseal, berberine is considered to be the primary pharmacologically active compound in goldenseal. Berberine's most common historic and clinical uses include bacterial diarrhea, intestinal parasites, and ocular trachoma infections. Berberine has been shown to exhibit significant antimicrobial activity against a variety of bacteria, fungi, protozoans, helminths, chlamydia, and viruses (Birdsall, 1997). Some berberine containing plants have been shown to produce substances which, by themselves, are completely without antimicrobial activity however, when used in conjunction with berberine, they enhanced the activity of berberine by as much as 2,500 times (Stermitz, 2000, Tegos, 2002). In addition to this antimicrobial activity, berberine has been found to have numerous pharmacological effects including antagonism of the effect of *cholera* and *E. coli* heat stable enterotoxin (Sack, 1982), delay of small intestine transit time (Eaker, 1989), inhibition of intestinal secretions (Zhu, 1983), significantly inhibit spontaneous peristalsis in the intestine (Birdsall, 1997), inhibition of smooth muscle contraction (Tai, 1981), potent inflammation inhibitory activity (Yesilada, 2002), inhibition of cyclooxygenase-2 (COX-2) transcriptional activity in a dose and time dependent manner (Fukuda, 1999), and inhibition of I1'-8 production in rectal mucosa in rats (Zhou, 2000). Furthermore, berberine has been shown to produce significant cardiovascular, cholesterol reduction, MAO inhibition, and antidiabetic activities. Berberine is considered to be a non-antibiotic anti-diarrheal drug (Baird, 1997).

Several recent studies have been conducted regarding the in vitro effectiveness of the antimicrobial constituents of goldenseal crude extract and its isolated alkaloids against a variety of oral and digestive tract pathogens including *Streptococcus mutans, Fusobacterium nucleatum*, and 15 strains of *Helicobacter pylori*. Results indicated the crude extract and isolated berberine to be very active against these pathogens (Hwang, 2003, Mahady, 2003).

In a 2001 study, the antibacterial activity of crude goldenseal extract and the isolated alkaloids berberine, hydrastine, and canadine were evaluated against five strains of microorganism: *Staphylococcus aureus* (ATCC 25 993 and ATCC 6538P), *Streptococcus sanguis* (ATCC 10 556), *Escherichia coli* (ATCC 25 922), and *Pseudomonas aeruginosa* (ATCC 27 853). The results of this study were reported to provide a rational basis for the traditional antibacterial use of goldenseal (Scazzocchio, 2001).

Berberine, isolated from the roots of goldenseal, was demonstrated to be responsible for the significant activity of goldenseal extract against multiple drug resistant *Mycobacterium tuberculosis* (Gentry, 1998)

A 1998 study conducted at Iowa State University entitled *Botanicals for Pigs—Goldenseal* compared goldenseal's use as a natural antimicrobial agent in nursery pigs with Mecadox. The study reported that growth of the pigs on a 1% goldenseal diet were often not statistically different from the Mecadox controls.

One significant thread common to the above studies is the fact that in each instance the activity of the crude extract was shown to be equal to or greater than the activity of isolated berberine. In one particular instance, Hwang (2003), the crude extract of goldenseal root and rhizome was demonstrated to have comparable activity to the isolated berberine even though the crude extract only contained 0.02% berberine, $\frac{1}{5000}^{th}$ the concentration of the isolated berberine. All other fractions and combinations of alkaloids produced only minimal activity and can not possibly account for the increased activity of the crude extract. This indicates there are other unknown compounds in goldenseal root and rhizome which are inactive by themselves but significantly enhance berberine's activity when combined. Accordingly standardization to specific quantities of berberine in a goldenseal product will most likely produce varying pharmacological activity due to year to year variations in environmental conditions which produce not only fluctuating amounts of berberine but also the unknown compounds.

This invention reveals a method of manipulating the concentration levels of goldenseal's primary marker compounds within the final product without adulteration of any kind. In addition, the invention goes a step further by revealing a method of quantifying the effects of the unknown compounds in goldenseal then using the aforementioned method to produce a goldenseal product which produces a predictable level of pharmacological activity.

SUMMARY OF THE INVENTION

Accordingly, it is a first object of the present invention to provide an improved method for isolating or obtaining herbal extracts.

Another object of the present invention is a method of manufacturing herbal extracts.

A still further object of the present invention is a method for isolating or obtaining herbal extracts that are economically attractive. In one aspect of the invention, the herbal extract is used to treat human and non-humans. Non-human, include but not limited to, farm animals such as chickens, pigs, cows, fish and others.

Yet another object of the invention is a method that produces herbal extracts with more predictable levels of pharmacological activity over prior art techniques.

One other object of the present invention is a method of making high concentration extracts in lower unit doses for patient use.

Other objects and advantages will become apparent as a description thereof proceeds.

BRIEF DESCRIPTION OF THE DRAWINGS

FIG. 1. Diagram of production Process.

FIG. 2. Relative Recoveries from three Methods of Drying One Pound of Fresh Goldenseal.

FIG. 3. Hydrastine/Berberine Content Goldenseal after Three Methods of Drying.

FIG. 4. Net effect of drying and grinding goldenseal on gross alkaloids extraction compared with fresh material.

FIG. 5. Alkaloid Extraction as a function of Alcohol Concentration.

FIG. 6. Combined hydrastine/berberine recovered from five different solvent levels over three extractions.

FIG. 7. Goldenseal Extraction Cost Optimization.

FIG. 8. Effect of sleep Hollow Farm GS on LDLR message in Hep G2 after 16 hrs.

DETAILED DESCRIPTION OF THE INVENTION

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

The term "composition", as used herein, refers to a mixture of components. As used herein, "components" refers to chemical compounds, salts of such compounds, complexes and other molecular and ionic species found in nature.

The term "herbal", as used herein, refers to plant substances. materials and/or parts.

The term "pharmaceutical grade" when used in this specification means that certain specified biologically active and/or inactive components in a botanical drug must be within certain specified absolute and/or relative concentration range and/or that the components must exhibit certain activity levels as measured by a disease-, disorder- or condition-specific bioactivity assay. The disease, disorder or condition may afflict a human or an animal.

As will be understood by those skilled in the art, the term "pharmaceutical grade" is not meant to imply that the botanical drug is applicable only to products which are regulated for example, those provided under prescription, i.e., "Rx" products or over the counter, i.e., "OTC". The term is equally applicable to products provided Rx, OTC or as a dietary supplement, i.e., "DSHEA".

All publications mentioned herein are incorporated herein by reference for the purpose of describing and disclosing the subject components of the invention that are described in the publications, which components might be used in connection with the presently described invention.

The information provided below is not admitted to be prior art to the present invention, but is provided solely to assist the understanding of the reader.

The details of one or more embodiments of the invention are set forth in the accompanying drawings and the description below. Other features, objects, and advantages of the invention will be apparent from the description and drawings, and from the claims.

One criticism traditionally charged to the use of herbal products as medicines is the absence of standard levels of biologically active materials from natural plants. The present invention provides both a method of obtaining standardized biological compositions having a desired level of pharmaceutical activity and a method of standardized processing procedures. The present invention also permits the isolation of biological compositions or components, and in particular herbal compositions or components, having high, or the highest pharmacological activity obtainable by a specific process, such as extraction.

In one aspect of this invention, the methods of the present invention used for standardization of a biologically or pharmacologically active mixture of chemical components obtained from a biological source, preferably a plant, involve initially conducting a plurality of different processes using a plurality of samples from the same biological source, preferably plant source, most preferably goldenseal, to produce a plurality of crude extracts. Physical and/or chemical tests are then performed on the crude extracts to provide qualitative and, in most instances, quantitative information regarding the chemical component(s) of the crude extracts. In one aspect of the invention, the crude extracts from these processes are combined, sampled, analyzed and then concentrated to a predetermined point. In one aspect of the invention, the samples are analyzed using an HPLC or alike. In one aspect of the invention, the samples are concentrated using an evaporator system in conjunction with vacuum or a like.

In one aspect of this invention, a method is provided for processing dried or fresh goldenseal produced from either wild collected, conventional cultivated, or certified organic sources or a combination thereof in order to produce a hydro-alcoholic tincture and/or a solid extract with consistent and predictable amounts of at least two goldenseal quality marker compounds, berberine and hydrastine as well as the bioactivity thereof. In one aspect of this invention, the preferred source is certified organic plant source which yields a 100% certified organic product as defined by the USDA NOP.

When the source of the mixture of the chemical components is a plant source, such as a mixture used in an herbal medication or composition, typical processes may include methods of harvesting, methods of storage, methods of expressing liquid components and, preferably, methods of extraction of chemical components, most preferably the chemical components responsible for pharmacological activity. A method is chosen for a particular process and variables are changed, when possible, one at a time to produce a plurality of method products.

The present invention is expected to have most widespread application to plant sources, in particular goldenseal.

In one aspect of this invention, the inventor has developed a process which allows the precise standardization of at least two marker compounds generally recognized as indicators for the quality of *Hydrastis canadensis* (goldenseal) which are believed to be the primary biologically active constituents, berberine and hydrastine, in both hydro-alcoholic tinctures and solid extracts of goldenseal. The process is suitable for use in, but not limited to, conventional and 100% certified organic production systems. This invention also reveals compositions of berberine and hydrastine, within the context of a whole plant goldenseal tincture or extract, which produce enhanced immune system activity in humans and/or animals. Furthermore, this invention reveals compositions of berberine and hydrastine, within the context of a whole plant goldenseal tincture or extract, which suppress growth and virulence factors of certain human, animal, and plant pathogens including but not limited to, *Bacillus cereus, Bacillus pumilus, Bacillus subtilis, Candida albicans, Candida glabrata, Candida tropicalis, Candida utilis, Chlamydia trachomatis, Corynebacterium diphthenae, Cryptococcus neoformans, Entamoeba histolytica, Escherichia coli, Fusobacerium nucleatum, Giardia lamblia, Helicobacter pylori, Klebsiella pneumoniae, Leishmaniasis* sp., *Microsporum gypseum, Mycobacterium tuberculosis, Pseudomonas aeruginosa, Shigella boydii, Sporotnchum schenkii, Staphylococcus aureus, Staphylococcus albus, Streptococcus sanguis, Streptococcus mutans, Strepococcus pyogenes, Trichomonas vaginalis, Trichophyton metangrophytes,* and *Vibrio cholera.*

In the method of the invention, the extraction solvent is preferably an ethanol and water mix but may be other solvents. A protocol using a known starting weight of the herbal material, a known volume of finished product to be obtained and a percentage of alcohol in the finished extract based on the herb to be processed can be used to initiate and guide the method.

Extracts, tinctures or the like produced by the inventive method can be used as is or combined with other extracts for medicinal purposes. In addition, one or more extracts can be utilized to make tonics for medicinal use.

The separatory procedure employed is preferably a chromatographic procedure such as high performance liquid chromatography (HPLC), thin-layer chromatography (TLC), high pressure thin layer chromatography (HPTLC). Capillary electrophoresis (CE) and UV/V is spectrophotometric methods can also be used.

Preferable detection systems in the case of HPLC, include absorbance and fluorometric spectroscopy, refractive index, electrochemical methods, evaporative light scattering, electrospray mass spectrometry, or a combination of these.

The botanical materials for the process can be fresh, fresh dried, or dried. The part of the plant used as the raw material can vary as well. Certain plants have most of the active principles in the roots while others may have the active principles in the leaves, and some have active principles in both. The present method is intended for use with all parts of the targeted plant, including flowers, leaves, stems, and roots combined in calculated percentages to produce pre-standardized raw material for extraction purposes.

The botanical material may be processed to form an aqueous or organic extract of the whole plant or a selected part of the plant. The botanical material can also be processed in whole or part to form a powder. Many of the botanicals of interest are commercially available as powders, aqueous extracts, organic extracts or oils. In one embodiment, extracts of the plant material are preferred because they are easier to dissolve in liquid pharmaceutical carriers. However, powdered plant materials are well-suited for many applications where the drug is administered in solid form, e.g., tablets or capsules. Such methods of producing these products are well known to those of skill in the art. Furthermore, many of the plant materials and/or extracts are available commercially however, plant material cultivated under USDA NOP certified wild simulated conditions is the preferred source. As examples of the cultivation, processing and extracting of botanicals the following examples are provided.

For a typical root, it may be sliced, frozen or pulverized. If powdered it is then shaken with an appropriate solvent and filtered. Alternatively, the following methods are used: the root is homogenized, ethanol extracted and filtered. The initial solvent extract from the methods above may be further extracted using liquid/liquid extraction with an appropriate solvent. Botanicals may also be processed as a paste or powder which may be cooked.

A variety of solvents may be used in the extraction process; for example acetone, acetonitrile, dichloromethane, ethyl acetate, ethanol, hexane, isopropanol, methanol, other alcohols, water, and supercritical carbon dioxide and mixtures thereof.

The dried material may be prepared in a variety of ways including freeze-drying, drying via microwave, cooling with liquid nitrogen and pulverizing; or air-drying in the shade, or with forced heated air at about 40° C.

The following is an example of a process to produce a 100% certified organic goldenseal liquid extract. The example is intended only for illustration purposes of the several aspects of the invention.

Raw goldenseal is available from a variety of sources. Wild collected, which accounts for approximately 95% of the raw goldenseal currently on the market, is the least desirable source due to goldenseal's endangered status and unknown contamination and/or adulteration with undesirable substances. Cultivated goldenseal is the preferred source with wild simulated cultivation in a natural forest environment in conformance with the USDA NOP (certified organic) most preferred. USDA NOP standards are incorporated in this specification in their entirety by reference.

Since goldenseal is primarily wild collected only limited information is available regarding optimal cultivation and almost none regarding optimal post-harvest handling methods. Wild simulated certified organic cultivation in a natural forest environment is the most preferred source of raw material therefore it was necessary to survey locations where goldenseal is native to determine optimal soil chemical characteristics for plantation establishment. Table 2 lists the soil chemical profiles for three native goldenseal sites as well as beginning soil chemical characteristics for a proposed certified organic goldenseal cultivation site before and 1 year after soil amendments were added.

Native site # 1 was located on public land in Walker county, Georgia on the eastern escarpment of the southern portion of the Cumberland Plateau. We were accompanied to the site by the Program Botanist of the Georgia Department of Natural Resources Plant Protection Program. The specific site was located in the bottom of a large sink approximately 2 acres in size which sloped gently to the east. The goldenseal population covered approximately one-fourth of the bottom area and extended 25 feet up the southern wall. Surface rock outcroppings were Mississippian aged limestones and conglomerates of the Monteagle formation. Tree canopy in the area was primarily tulip poplar, hickory, and maple with an occasional white or red oak.

The Walker county site was the largest visited, consisting of an estimated 10,000 plants. Approximately 25% of the plants were producing fruit. These plants appeared to be vigorous and no damage from pests or disease were detected.

Site # 2 was located in a private nature preserve in Hall county, Georgia just east of the Brevard Fault at the head of the Oconee river basin. We were accompanied to the site by the Supervisor and Head Biologist of the preserve. The goldenseal populations at this site were located in the bottom and 10 to 15 feet up the slopes of a steep ravine, draining to the southwest. Surface rock outcroppings were Pre-Cambrian Gneiss and Schists. These populations were in small groups of 10 to 100 plants each. Approximately 10% of the plants were producing fruit. They appeared to be vigorous and free of disease or pest damage. Tree canopy here was poplar, beech, and white oak.

Site # 3 was located in Overton county, Tennessee on private property, in the eastern section of the Western Highland Rim province of Tennessee, just west of the Cumberland Plateau in the Cumberland River drainage basin. We were accompanied to the site by the landowner. The plants at this site were also in small batches of 10 to 100 plants each. These were the most vigorous of any of the other sites and approximately 50% of the plants were producing fruit. Canopy cover in the area was primarily poplar, beech, hickory, oak, and an occasional cedar.

Application of dolomite to the soil at the proposed site, at a rate of 18 pounds per 100 square feet, resulted in a significant increase in soil pH from 4.7 to 6.2 (Table 2). Consequently, the level of P, K, Ca, Mg, Cu, Fe, and Na increased from those observed in the sample taken in 2001. The Ca and Mg levels showed a marked increase from soil with pH 4.7 to a soil with a pH of 6.2. This enabled us to bring the soil pH and other parameters at SHF within the range of those soils from the native locations.

The areas to be used for the wild simulated certified organic goldenseal beds are first cleared of only as much undergrowth as necessary to allow the use of a roto-tiller to prepare beds and to effectively maintain the beds once established. A small tractor with backhoe attachment can be used for the removal of small stumps. Light values are measured in the open and under the canopy with a Sunfleck Ceptometer or like instrument. The values are compared and the larger hardwood trees pruned to achieve an average 66% shade.

TABLE 2

Soil Chemical Properties at Three Native Goldenseal Locations and Sleepy Hollow Farm.

| | Location | | | | |
|---|---|---|---|---|---|
| | | | | Sleepy Hollow Farm | |
| Parameter | Walker[1] | Hall[2] | Overton[3] | May 31, 2001 | Amended May 31, 2002 |
| pH | 6.0 | 6.5 | 6.4 | 4.7 | 6.2 |
| Organic Matter (%) | 2.6 | 1.8 | 2.4 | 3.1 | 2.3 |
| Phosphorus (ppm) | 11 | 3 | 28 | 9 | 20 |
| Potassium (ppm) | 113 | 180 | 135 | 53 | 73 |
| Calcium (ppm) | 1549 | 1184 | 978 | 189 | 983 |
| Magnesium (ppm) | 101 | 204 | 72 | 47 | 334 |
| Sulphur (ppm) | 35 | 25 | 26 | 15 | 15 |
| Boron (ppm) | 0.6 | 0.8 | 0.8 | 0.3 | 0.4 |
| Copper (ppm) | 1.3 | 2.1 | 1.4 | 0.6 | 1.6 |
| Iron (ppm) | 75 | 69 | 129 | 118 | 124 |
| Manganese (ppm) | 319 | 138 | 181 | 124 | 128 |
| Zinc (ppm) | 4 | 3 | 20 | 2 | 2 |
| Sodium (ppm) | 20 | 19 | 19 | 17 | 23 |
| CEC | 11.8 | 10.9 | 7.2 | 7.1 | 10.4 |
| CS - K % | 2.5 | 4.2 | 5.3 | 2.1 | 1.8 |
| Ca % | 65.8 | 54.4 | 66.1 | 14.0 | 47.4 |
| Mg % | 7.2 | 15.6 | 8.3 | 5.8 | 26.8 |
| H % | 23.6 | 24.9 | 19.2 | 76.8 | 22.9 |
| % Na | 0.7 | 0.8 | 1.2 | 1.4 | 1.0 |
| K:Mg Ratio | 0.35 | 0.27 | 0.64 | 0.35 | 0.07 |

Sampling date:
[1]May 17, 2001;
[2]Jun. 14, 2001;
[3]Jun. 19, 2001.
4: Mean comparisons between locations for sampling dates in 2001 only.
CEC: Cation exchange capacity.
CS: Cation saturation.

Once the area is prepared, beds 4 foot wide are roto-tilled to a depth of 4 to 6 inches and the soil amended with composted leaves and other organic additives, as described above, based on native soil test results. Native conditions are further simulated by raking the dry leaves and other debris back on the top of the soil after planting. Length of the beds is dependent upon topography and tree location.

Wild simulated certified organic goldenseal plantations can be established using either seed or, the preferred method, vegetative propagation such as rhizome division or in vitro tissue culture. An example of vegetative propagation by rhizome division is to divide one pound of goldenseal rhizomes by breaking or cutting into approximately 100-4.5 gram pieces. Each piece should have at least one growth bud and one attached root. These pieces are then planted in the beds described above at a depth of approximately 3 to 4 inches using 6 inch spacing in each direction yielding 4 plants per square foot. These plants are then allow to grow for a minimum of four years. Cultivation for a period of at least 4 years meets CITES regulations and permits export of the rhizomes outside the U.S.

Selective harvesting of the various plant parts based on whether the individual plant is reproductive or sterile permits standardization of the raw material by combining the parts in calculated amounts to arrive at pre-determined levels of alkaloid concentration. Table 3 lists the berberine/hydrastine levels of the various parts of goldenseal, rhizome, root, leaf, and stem cultivated using the preferred method. Table 4 lists the berberine/hydrastine levels cultivated outside of the parameters defined by the preferred method of this invention. In addition the alkaloid content of the various plant parts of seed producing plants is also compared with that of non-seed producing or sterile plants.

As reflected in the proposed USP standards for goldenseal powder, the berberine content of goldenseal is normally found to be greater than the content of hydrastine. However, as indicated by the tables below, our research has shown significant differences between not only the total alkaloid content of reproductive plants vs sterile plants but also in the ratio of berberine to hydrastine. The ratio of berberine to hydrastine is reversed in sterile plants. Sterile plants produce a greater amount of hydrastine compared to reproductive plants. In addition, the leaf produces a greater amount of hydrastine than berberine with sterile plants producing roughly 50% more than reproductive plants. Furthermore, hydrastine is generally below detectable levels in the stem.

TABLE 3

Alkaloid content of reproductive goldenseal plant parts compared with sterile plants soil pH > 6.0

| Reproductive Plant Part | Berberine % Dry weight | Hydrastine % Dry Weight | Combined Alkaloid % |
|---|---|---|---|
| Rhizome | 5.51% | 4.85% | 10.36% |
| Root | 3.58% | 2.02% | 5.60% |
| Leaf | 0.65% | 0.93% | 1.58% |
| Stem | 0.98% | absent | 0.98% |
| Sterile Plant Part | Berberine % Dry weight | Hydrastine % Dry Weight | Combined Alkaloid % |
| Rhizome | 2.76% | 3.17% | 5.93% |
| Root | 0.99% | 1.62% | 2.61% |
| Leaf | 0.84% | 1.44% | 2.28% |
| Stem | 0.79% | absent | 0.79% |

TABLE 4

Alkaloid content of reproductive goldenseal plant parts compared with sterile plants soil pH < 5.0

| Reproductive Plant Part | Berberine % Dry weight | Hydrastine % Dry Weight | Combined Alkaloid % |
|---|---|---|---|
| Rhizome | 3.24% | 3.24% | 6.48% |
| Root | 2.73% | 1.96% | 4.69% |
| Leaf | 1.28% | 1.95% | 3.23% |
| Stem | 1.20% | absent | 1.20% |
| Sterile Plant Part | Berberine % Dry weight | Hydrastine % Dry Weight | Combined Alkaloid % |
| Rhizome | 1.98% | 2.24% | 4.22% |
| Root | 1.55% | 0.80% | 2.35% |
| Leaf | 0.68% | 1.50% | 2.18% |
| Stem | 0.99% | 0.22% | 1.21% |

Current production practices make no differentiation between reproductive or sterile plants when harvesting however, based on the above data, it is apparent that by selective harvesting of goldenseal based on whether the individual plant is reproductive or sterile and separation of the various plant parts, the resulting raw material can be standardized to either a desired ratio of berberine to hydrastine or specific levels of both by a calculated mixture of the various parts and/or reproductive or sterile plants. This method will produce pharmaceutical grade goldenseal raw material (dry powder after grinding) suitable for use in teas, capsules, and/or tablet manufacture. The standardized powder is also forms an excellent starting point for standardized tincture or extract production.

It is very easy to differentiate between reproductive and sterile plants when harvesting since reproductive plants produce a forked stem with two leaves, a flower, and a bright red raspberry like fruit. Sterile plants do not produce forked stems and only produce one leaf per stem. Therefore selective harvesting of reproductive and sterile plants is the preferred method of harvesting goldenseal to be utilized in this invention.

Selective harvesting of the stem and leaf is relatively simple, first the plant is identified as being either reproductive or sterile as described above then the stem is cut (either manually or mechanically) at ground level. The leaf is separated from the stem by cutting or pulling, then the parts are placed and held in separate labeled containers until needed for determination of alkaloid content by one of the methods described below and then further processing. If the root and rhizome are not to be harvested at the same time, a colored marker, example red for reproductive plants and green for sterile, is placed in the bed location of the plant so it can be identified at a later time.

The rhizome and root are harvested either manually or mechanically by loosening the dirt surrounding the rhizome and root then removing them from the ground. The rhizome and root are identified as either reproductive or sterile then placed in labeled containers. After harvesting the goldenseal is prepared for drying by placing the material on wire mesh screens and washing with potable water to remove soil and debris.

Separation of the root and rhizome is accomplished by drying the material then placing the material in a cylindrical container. The container is rotated which tumbles the material similar to a clothes dryer. This tumbling causes the roots to break off the rhizome. The material is then screened using a mesh size which permits the smaller pieces of the root to pass through but retains the larger rhizome.

Fig. 1 illustrates the recovery rates from various methods of drying. There are significant differences in recovery between the sun dried and shade dried when compared to the material from the controlled drier, 32% and 33% vs. 27% respectively. This difference is attributed to more complete drying from the controlled drier. Scores from the visual appearance, texture, and odor ratings revealed material from the controlled drier to be the most desirable, followed by the sun dried with the shade dried being the least desirable. The control dried material has a darker more distinct color, a firmer snap, and a slightly stronger odor than the other two methods. The sun dried material is very close to the controlled dried with the exception that the color is somewhat lighter. The shade dried material is less firm and noticeably lighter in color.

TABLE 5

| | Hydrastine % | Berberine % | Total % | Total Grams |
|---|---|---|---|---|
| 1 lb. Fresh | 1.05% | 1.04% | 2.09% | 9.48 |
| Sun Dried | 3.34% | 3.82% | 7.16% | 10.39 |
| Shade Dried | 3.17% | 3.44% | 6.61% | 9.90 |
| Controlled Drier | 3.24% | 3.78% | 7.02% | 8.60 |

The sun dried and the controlled drier produces total hydrastine/berberine percentages which are not significantly different however, there are significant differences between both the sundried (7.16%) and the control dried (7.02%) goldenseal and the material which was shade dried (6.61%). This percentage was then applied to the recovery factor from the drying methods in order to determine the total grams of alkaloids produced from each pound of fresh goldenseal. Even though the control dried material compared favorably with the sun dried material in terms of percentage of combined alkaloids, the actual amount of alkaloids produced from one pound of fresh goldenseal was significantly greater in the sun dried samples 10.39 grams vs. 8.60 grams from the control dried samples, a 17% difference. The sun dried material produced the greatest amount of hydrastine and berberine therefore sun dried material is the preferred method of drying for this invention.

TABLE 6

| | Sun Dried | Shade Dried | Controlled Drier |
|---|---|---|---|
| Ground Dry | 7.50% | 6.78% | 3.37% |
| Ground Frozen | 4.91% | 4.12% | 2.71% |
| Ground Frozen/Thawed | 4.38% | 3.77% | 3.17% |

Table 6 details the percentage of raw material lost during the grinding process. There were significant differences between the various methods of grinding with the material from the controlled drier posting the least amount of loss in each method of grinding with the control dried ground frozen category performing best with a loss of 2.71% and the sun dried ground dry category the worst with a 7.50% loss. The rather high results posted by the sun and shade dried, ground dry material can most likely be attributed to mill operator inexperience however, even when allowing for this the controlled drier material still significantly outperformed the other drying methods, exhibiting less tendency for caking and packing while producing a somewhat brighter color end product.

TABLE 7

| | Sun Dried | Shade Dried | Controlled Drier |
|---|---|---|---|
| Dry | 7.12% | 6.82% | 6.96% |
| Frozen | 7.21% | 6.95% | 7.65% |
| Froz/Thaw | 7.16% | 6.64% | 7.46% |

Table 7 contains a listing of the total hydrastine/berberine concentration in each sample after the grinding process was complete. Grinding while frozen consistently produced a higher percentage of alkaloid content than the other treatments. The frozen and frozen/thawed treatments produced a greater total alkaloid percentage in the sun dried and control dried categories than the dry material which was ground without any additional treatment. The control dry frozen sample produced the highest percentage alkaloid content, 7.65%, while the shade dried frozen/thawed sample was the lowest at 6.64%.

TABLE 8

| | Sun Dried | Shade Dried | Controlled Drier | Fresh |
|---|---|---|---|---|
| Before Grinding | 10.39 gr | 9.90 gr | 8.60 gr | 9.48 gr |
| Grnd. Dry | 9.55 gr | 9.52 gr | 8.23 gr | |
| Grnd. Frozen | 9.95 gr | 9.97 gr | 9.11 gr | |
| Grnd. Froz/Thaw | 9.93 gr | 9.56 gr | 8.84 gr | |

Table #8 displays the net effect of the various treatments on the amount of hydrastine/berberi ne available for extraction from one pound of fresh goldenseal. This was calculated by multiplying the weight of the fresh material times the percentage of recovery after drying times the percentage of recovery after grinding times the percentage of alkaloid content of the final product. The sun dried and shade dried methods produced results which were not significantly different however, both were significantly better than the results produced by the controlled drier method. Shade dried ground frozen produced the greatest amount of alkaloids per pound of starting material but it was not significantly different from the other shade or sun dried treatments. The controlled drier performed the poorest. FIG. 3 is a visual presentation of those results when compared with starting fresh material. Therefore grinding while frozen is the preferred method of grinding goldenseal for this invention.

Purchased powdered goldenseal, HPLC 2.624% hydrastine, 3.269% berberine, was used to develop the liquid extraction method. FIG. 4 visually illustrates the relative amounts of combined hydrastine/berberine recovered from the above goldenseal powder using solvents with five different concentrations of 95% ethanol and water. Total alkaloid recovery was greatest from the 1:3:1 (goldenseal:95%ethanol:water) solvent mixture and lowest from the 1:0:4 or 100% water solvent. An optimum concentration level was apparent at approximately 60% ethanol.

The second extraction produced a somewhat flatter curve than the first. The 1:3:1

TABLE 10

| Optimal Solvent Concentration | | | |
|---|---|---|---|
| Ethanol:Water Concentration | % Alk Ext 1 | % Alk Ext 2 | % Alk Ext 3 |
| 4:0 | 0.775 | 0.302 | 0.322 |
| 3:1 | 1.144 | 0.397 | 0.244 |
| 2:2 | 1.102 | 0.361 | 0.171 |

TABLE 10-continued

Optimal Solvent Concentration

| Ethanol:Water Concentration | % Alk Ext 1 | % Alk Ext 2 | % Alk Ext 3 |
|---|---|---|---|
| 1:3 | 0.844 | 0.354 | 0.135 |
| 0:4 | 0.615 | 0.322 | 0.213 | solvent mixture again produced the highest total concentration of combined alkaloids. The third extraction, in which the solvent concentrations were reversed, was designed to capture any alkaloids not recovered by its reciprocal concentration. The 1:4:0 solvent concentration is preferred for the third extraction. The overall results indicated that the solvent concentration levels with the lesser amounts of ethanol recovered a lower percentage of alkaloids except for the 1:4:0 concentration level which was not a great as the 1:3:1 level with an approximately 60% ethanol concentration appearing to be the optimal.

This concentration level was then used to produce a liquid goldenseal extract from goldenseal which had been sun dried and ground while frozen. The beginning alkaloid content of this material as measured by HPLC was 3.337% hydrastine and 3.822% berberine for a combined total of 7.159%. Utilizing the same procedure as above 12 ounces of liquid goldenseal extract was produced and spectrophotometrically determined on-farm to contain 0.62% hydrastine and 0.60% berberine, total 1.22%. This crude extract was then concentrated 3:1 and reanalyzed revealing a 1.89% hydrastine and 1.72% berberine content, total 3.61%.

Data from the above experiments was analyzed and the following table constructed to illustrate the relative cost effectiveness of each solvent concentration. The solvent from each of the 5 concentration levels used for the initial extraction was combined with the respective solvent from the other two extractions yielding 12 ounces of liquid extract containing a combined hydrastine/berberine concentration as shown in the table above. This number was then converted to the number of ounces of extract if it contained 1% alkaloids. Cost for the ethanol/water used was calculated based on actual cost, maintaining a 25% ethanol level after concentration as a preservative. The cost for goldenseal was the price we paid for the goldenseal used to develop the process, $64 per pound. The combination of these two factors produced a total cost for the batch. That number was then divided by the number of ounces @ 1% alkaloids for each batch to produce the final cost per ounce for each of the five ethanol/water concentration levels.

TABLE 12

Final Cost

| Ethanol:Water Concentration | Combined %12 ozs. | ozs. @ 1% Alkaloids | Cost for etoh/h$_2$o | Cost for goldenseal | Total Cost | Cost per oz. per 1% |
|---|---|---|---|---|---|---|
| 3:2 | 0.600 | 7.20 | $0.68 | $4.47 | $5.15 | $0.72 |

This model was then used to develop a cost per ounce of raw materials used to produce the liquid extract from Sleepy Hollow Farm's material. The cost for the goldenseal was based on a price of $10 per 1% alkaloid content per pound. We believe this method of pricing to be much more representative of the value of any particular goldenseal lot for both the grower and the bulk buyer. This is equivalent to the current market for cultivated goldenseal of $35 per pound with a 3.5% minimum alkaloid content and yields a cost per pound slightly more than that paid for the previous material, $71.59/lb for SHF goldenseal compared with $64/lb from a distributor. The final cost per ounce of liquid goldenseal extract containing 1% alkaloids produced from Sleepy Hollow Farm's harvest was comparable with that from the purchased material even though the assumed cost per pound was higher due to its higher alkaloid content.

To summarize the method, powdered goldenseal, produced as described above utilizing wild simulated cultivation methods certified as meeting the standards of the NOP by a third party certifier authorized by the USDA, is sun dried then ground while frozen. The powdered goldenseal is then combined with a solvent mixture consisting of about 60% certified organic grain alcohol (95% ethanol) and about 40% water in

TABLE 11

Extraction Cost Optimazation

| Ethanol: Water Conc. | Total % Ext 1 | Total % Ext 2 | Total % Ext 3 | Combined % 12 ozs. | ozs. @ 1% Alkaloids | Cost for etoh/h$_2$o | Cost for goldenseal | Total Cost | Cost oz./1% |
|---|---|---|---|---|---|---|---|---|---|
| 4:0 | 0.775% | 0.302% | 0.322% | 0.466% | 5.59 | $0.53 | $4.00 | $4.53 | $0.81 |
| 3:1 | 1.144% | 0.397% | 0.244% | 0.595% | 7.14 | $0.67 | $4.00 | $4.67 | $0.65 |
| 2:2 | 1.102% | 0.361% | 0.171% | 0.545% | 6.54 | $0.61 | $4.00 | $4.61 | $0.71 |
| 1:3 | 0.844% | 0.354% | 0.135% | 0.444% | 5.33 | $0.50 | $4.00 | $4.50 | $0.84 |
| 0:4 | 0.615% | 0.322% | 0.213% | 0.383% | 4.60 | $0.43 | $4.00 | $4.43 | $0.96 | a ratio of 1 part goldenseal powder by weight to 4 parts solvent mixture by volume in a suitable container. The container is constantly agitated by either shaking or using a motorized mixer with paddles attached which rotate at a speed of approximately 60 to 120 rounds per minute for 24 to 72 hours. The mixture is then filtered and the liquid reserved in a separate labeled amber glass container while the once extracted goldenseal is returned to the extraction container. The container is then refilled with the same quantity of the ethanol/water mixture as before and the procedure repeated. The mixture is filtered a second time and the liquid again reserved in a separate labeled container. The twice extracted goldenseal is then returned to the extraction container which is refilled with fresh solvent mixture containing 100% certified organic grain alcohol (95% ethanol). The process is repeated, then mixture filtered for a third time and the liquid reserved in a separate labeled container.

SHF's extraction process was developed through our USDA SBIR projects and is the resource which facilitates our ability to produce products with consistent chemical marker levels. This process has been third party certified to be in compliance with the USDA NOP standards by Oregon Tilth, Inc. An example of the process is illustrated below with data from SHF batch # 1004. Fresh *Hydrastis* root and rhizome (root) was harvested from SHF's USDA NOP certified plantation. After harvesting the material was placed on wire mesh screens and washed with potable water to remove soil and debris. The material was then dried on sanitized trays in a controlled atmosphere at 105° F. until approximately ⅔ of the initial weight was lost. This lot was identified through the various processes by the assignment of a lot number which can be tied back to the organic certification records which begin with the source of the seed and/or planting stock and a land use history for at least three years immediately prior to planting. Based on optimal data from our previous research, the *Hydrastis* root was then frozen for 24 hours at 0° F., then reduced in size in a mill so that all of it will pass through a 40 mesh screen. It was then HPLC verified by our cooperators at Rutgers University to contain 3.34% hydrastine and 3.82% berberine. The raw *Hydrastis* was extracted by maceration for 24 hours at room temperature with intermittent agitation three times utilizing fresh solvent each time. The solvent consisted of a mixture of USDA NOP certified/USP ethanol and water averaging 55% ethanol and 45% water and was used at a ratio of 1:12 (w:v) for the first extraction and 1:8 (w:v) in subsequent extractions.

| SHF's Chemical Marker Standardization Process Calculation Batch # 1004 | | | | | |
|---|---|---|---|---|---|
| Extraction # | Hydrastine mg/ml | Berberine mg/ml | Total mg/ml | Hyd/Ber Ratio | Amount Used ml |
| 1 | 2.07 | 2.24 | 4.31 | 0.92 | 550 |
| 2 | 1.34 | 1.52 | 2.86 | 0.88 | 475 |
| 3 | 0.34 | 0.48 | 0.82 | 0.70 | 500 |
| Final Product | 1.19 | 1.33 | 2.52 | 0.88 | 1525 |

Each extraction was then filtered through a 2.5 µm glass fiber filter, a sample taken for HPLC analysis, then stored in hermetically sealed, amber glass, food grade containers. Results of those analyses are presented below. Once the hydrastine/berberine level in each extraction is known it is then possible to calculate quantities of each extraction which will equal a desired concentration. The goal of this batch was 2.5 mg/ml combined hydrastine/berberine with a hydrastine/berberine ratio of 0.8. The material to be used in this project will meet these standards ±10%.

Solid extracts are produced by utilizing a crude liquid *Hydrastis* extract as described above then the crude extract is evaporated in a water bath rotary evaporator at 40° C. and a vacuum of 20" Hg to produce a solid *Hydrastis* extract with approximately equal levels of berberine/hydrastine. Samples will be taken for HPLC analysis, the extract is then stored in hermetically sealed, amber glass, food grade containers.

Current state of the art would, at this point, combine the solvent mixtures from the above extractions, take samples of the combined mixture and subject them to HPLC analysis, then dilute or concentrate the mixture in order to obtain a desired level of either berberine, hydrastine, or a combination of both expressed as "total alkaloids". The method of this invention is through an added step in the process which will allow standardization to specific levels of both berberine and hydrastine. Details of that additional step follow:

The crude extracts from the above process are combined, samples taken and HPLC analysis performed, and then concentrated 3:1 using a water bath evaporator at approximately 40 EC and vacuum of 20 inches Hg. This concentration removes all the ethanol from the mixture. Since hydrastine is not very soluble in water it begins to precipitate out of the mixture once the ethanol is removed while the berberine remains in solution. This precipitation is monitored and once the hydrastine level reaches a predetermined point, non-limiting example, exactly 2 parts berberine/1 part hydrastine, the mixture is decanted and then diluted with certified organic grain alcohol (95% ethanol) to obtain the desired level of standardization. If a hydrastine rich product is desired, 1 part berberine/2 parts hydrastine as a non-limiting example, the hydrastine is allowed to precipitate to a predetermined point, then a calculated percentage of the berberine rich solution is decanted, the remaining mixture containing the hydrastine precipitate is then diluted with a calculated volume of certified organic grain alcohol (95% ethanol), the mixture thoroughly blended and the hydrastine precipitate reintroduced into the mixture. If a solid extract is desired, the mixture would then be evaporated to dryness using a water bath evaporator, spray drying, or other method of drying. The resulting product can be very precisely standardized to the content of both hydrastine and berberine.

The method permits the preparation of a pharmaceutical grade combination of hydrastine and berberine, where the practitioner or researcher selects the relative proportions of the two ingredients. This process is a major step up in the quality of goldenseal tinctures and extracts and can be used to produce pharmaceutically accurate combinations of active ingredients from goldenseal and other plants which have medicinal value.

A schematic diagram for goldenseal standardized extract process is presented in the drawing section. This is intended only for illustration purposes of the several aspects of the invention.

HPLC Method of Hydrastine/Berberine Determination in Goldenseal.

Principle: Hydrastine and Berberine, two major alkaloids in goldenseal are extracted from herbs and herb extracts using acidic aqueous methanol solution. They are then quantitated by isocratic HPLC at 235 nm using a reversed phase column.

Equipment: HP 1100 Chromatograph (or equivalent) equipped with the following:
Auto sampler.
UV Detector capable of 235 nm.
Column—Luna phenyl-hexyl 150*4.6 mm, 5_M, Phenomenex
Data Acquisition—HP Software or equivalent.
Materials:
Acetonitrile —HPLC grade (EM Science).
Isopropanol —HPLC grade (EM Science).
Phosphoric acid 85% (Fisher)
Water HPLC grade (Fisher Scientific).
Extraction solvent: 50% methanol acidic solution: mix 250 ml methanol and 250 ml water, and 10 mL concentrated HCl.
Sodium Dodecyl Sulfate, HPLC grade from Fisher.
1R, 9S)-β-hydrastine standard from Sigma Chemical Co.
Berberine standard from Sigma Chemical Co.
Mobile Phase: 40% acetonitrile+10% Isopropanol+0.2% phosphoric acid+5 mM Sodium Dodecyl Sulfate.

To prepare 1 Liter, measure ~400 mL HPLC grade water in a 1000 mL graduated cylinder and add 1.44 g Dodecyl Sodium Sulfate to it. In a separate 500 mL graduated cylinder, measure 400 mL of acetonitrile and add to the solution. In a separate 100 mL graduated cylinder, measure 100 mL of isopropanol and add to this solution. Add 2 mL phosphoric acid to this solution. Dilute to volume with HPLC grade water and mix well.

HPLC Condition:

The following HPLC conditions were used when carrying out this analysis:
Instrumental Assay Parameters:
Flow Rate: 1.2 mL/min.
Wavelength: 235 nm.
Injection Volume: 10 μL.
Run Time: 12 min.
Hydrastine Elution Time—Approximately 4.0 minutes.
Berberine Elution time B Approximately 7.6 minutes
Preparation of Standard Solution:

Accurately weigh about 15 mg Hydrastine chloride and 15 mg Berberine chloride into 25 mL volumetric flask, record the weight (important: correcting for water and HCl) Add approximately 15 mL 50% methanol acidic solution and sonicate for 15 minutes. Allow the flask to cool to room temperature and fill to full volume with 50% methanol acidic solution.

Measure 5 mL above solution and transfer to a 25 mL volumetric flask and diluted to the full volume using 50% methanol acidic solution (standard solution).

Preparation of Samples:

For herbs, accurately weigh about 40 mg powder into a 15 mL centrifuge tube Add 14 mL of 50% methanol acidic solution and sonicate for 30 min.

Centrifuge for 10 minutes. Put 1 mL clear solution into HPLC vial for analysis For liquid sample, Pipet 0.5 mL into 15 mL volumetric flask, dilute to 14 mL using extraction solution.

Centrifuge for 10 minutes. Put 1 mL clear solution into HPLC vial for analysis

Calculation and Reporting of Results:

The two alkaloid contents in a sample are calculated using the following equation are reported as each individual one:
alkaloid=
$P_u$=Peak area of each alkaloid in the sample.
$P_s$=Peak area of alkaloid in the standard.
$C_s$=concentration of each free alkaloid in the standard (g/mL).
$W_u$=Weight of the sample (g).
50=volume of sample (mL), 100=converts to percent.

Alternative UV/V is Spectrophotometric Method

Two buffer solutions were prepared by mixing appropriate amounts of citric acid (Fisher) and dibasic sodium phosphate (Fisher) in de-ionized ultra-filtered water (DIUF) (Fisher) to achieve pH of 5.6 and 7.2.

A berberine stock solution was prepared by dissolving 0.25 g of berberine hydrochloride hydrate 97% (Fisher) in 100 ml DIUF water. A berberine reference solution (1.25 mg %) was prepared by diluting 0.5 ml of the stock solution to 100 ml with 1 N HCl (Fisher).

A hydrastine stock solution was prepared by dissolving 0.2 g (1R, 9S)-β-hydrastine (Sigma) in 100 ml 1 N HCl. A hydrastine reference solution (4 mg %) was prepared by diluting 2 ml of the stock solution to 100 ml with 1 N HCl.

A bromocresol purple solution was prepared by dissolving 50 mg of the dye (Fisher) in a few drops of 0.1 N HCL and bringing the solution to 100 ml with DIUF water.

Berberine Determination: 0.5 ml of the crude goldenseal extract, prepared using the process developed above, is diluted to 100 ml with pH 7.2 buffer. A 10 ml aliquot is transferred to a 60 ml separator containing 10 ml chloroform (Fisher) and 1 ml of the bromocresol purple dye solution. The mixture is shaken for 1 minute and the layers allowed to separate completely.

The chloroform layer is transferred to a second 60 ml separator and the remaining aqueous layer re-extracted with an additional 10 ml chloroform. The combined chloroform extracts are shaken for 15 seconds with 10 ml 0.1 N NaOH (Fisher) to release the combined dye. The aqueous layer is then transferred to a beaker and diluted to 25 ml with DIUF water. A sample of the final solution is transferred to a 1 cm cell and placed into a Genesys 10 UV/V is spectrophotometer with additional cells containing the berberine reference solution and a blank containing 1 N HCl. The absorbencies are measured at 590 nm and recorded.

The concentrated (3:1) goldenseal extract is analyzed for berberine in the same manner as above except 3 ml of the dye solution is used and the final solution diluted to 50 ml with DIUF water in order to get a reading within the limits of the machine.

Hydrastine determination: 1.0 ml of the crude goldenseal extract, prepared using the process developed above, is diluted to 100 ml with pH 5.6 buffer. A 10 ml aliquot is transferred to a 60 ml separator containing 10 ml chloroform (Fisher) and 1 ml of the bromocresol purple dye solution. The mixture then shaken for 1 minute and the layers allowed to separate completely.

The chloroform layer is transferred to a second 60 ml separator and the extraction repeated with 2×10 ml chloroform. The combined chloroform extracts are shaken for 15 seconds with 10 ml 0.1 N NaOH (Fisher) followed by 5 ml saturated sodium chloride solution (Fisher). The chloroform layer is then evaporated just to dryness. The residue is dissolved in 1 N HCl, transferred to beaker and diluted to 25 ml. The absorbencies of the final solution together with the hydrastine reference solution is measured concomitantly in 1-cm cells at 345 nm with Genesys 10 UV/V is spectrophotometer using 1 N HCl as a blank.

The concentrated (3:1) goldenseal extract is analyzed for hydrastine in the same manner as above except 3 ml of the dye solution is used and the final solution is diluted to 50 ml with DIUF water in order to get a reading within the limits of the machine.

Standardization to Biological Activity

The following is an example of a method for standardizing the mixture of pharmacologically active mixtures of chemical components to antimicrobial activity. The example is intended only for illustration purposes of the several aspects of the invention.

Briefly, a sample from a combined extract lot as prepared above is taken and subjected to HPLC analysis to determine the berberine concentration therein. Another sample is taken and used to determine the minimum inhibitory concentration (MIC) and/or minimum bactericidal concentration (MBC) of the crude extract against a specific microorganism. MIC and/or MBC for a berberine reference standard is obtained at the same time. The procedures for making this determination are detailed after the following discussion. The results of these analyses are recorded.

The MIC (or MBC) of the berberine reference standard is divided by the MIC (or MBC) of the crude extract resulting in an "Activity Factor". An "Activity Factor" of 1 means the activity of the crude extract and the reference standard are equal, greater than 1 means the crude extract has greater activity than the standard and less than 1 means the crude extract has a lesser activity than the standard. (See Formula 1 below) The "Activity Factor" can be used as a standard to compare the activity of different batches or other manufacturers products against the same organism.

The reciprocal of formula 1, MIC (or MBC) of the crude extract divided by the MIC (or MBC) of the berberine reference standard yields a "Catalyst Factor". This number quantifies the effect of the unknown compounds which enhance the activity of berberine and is used in conjunction with the HPLC analysis of the crude extract to calculate the concentration of berberine in the crude extract necessary to produce activity equivalent to the reference standard or a fraction or multiple thereof as desired. (See Formula 2 below)

Once the concentration of berberine in the crude extract necessary to equal the activity of the standard is known, the crude extract can be standardized to a desired "Activity Factor" by manipulating the berberine level to a desired multiple or fraction of the standard.

CF=Catalyst Factor, quantifier of the effects of the unknown compounds
AF=Activity Factor, berberine reference standard=1
$AF_{target}$=Desired Activity Factor
$MIC_{extract}$=MIC of the crude extract against a specific organism, µg/ml
$MIC_{berberine}$=MIC of the berberine reference standard against a specific organism, µg/ml
$\%_{berberine}$=Concentration of berberine in the crude extract
$\%_{required}$=Concentration of berberine required to equal the activity of berberine reference standard
$\%_{final}$=Concentration of berberine in final product required to produce $AF_{target}$ $(MIC_{berberine}/MIC_{extract})=AF$  Formula 1

Example data from Hwang (2003) MIC of berberine and crude goldenseal root and rhizome extract against *Streptococcus mutans*

125/250=0.5

$(MIC_{extract}/MIC_{berberine})=CF$

250/125=2  Formula 2

$CF \times \%_{berberine} = \%_{required}$  Formula 3

2×0.02%=0.04% berberine concentration in the crude extract required to equal the biological activity of the berberine reference standard.

$AF_{target} \times \%_{required} = \%_{final}$  Formula 4

Assuming an arbitrary $AF_{target}$ of 5 times the standard:
5×0.04%=0.20% final berberine concentration to yield a product with 5 times the activity of the reference standard.

The extract is then standardized to the desired Activity Factor by manipulating the level of berberine using the process as previously described in the above examples.

The same procedure can be used to standardize to other pharmacological activities by substituting the appropriate test of pharmacological activity for the MIC/MBC tests. The use of multiple assays such as antimicrobial, antiproliferative, and anti-inflammatory allows for broad spectrum standardization Since the synergistic and/or additive compounds in *Hydrastis* produce increased activity, it is also possible that synergistic and/or additive toxicity could be produced therefore it is necessary to evaluate the toxicity of each formulation by utilizing the same assays as above except "friendly" organisms and normal tissue are used.

Once the data from the above studies has been obtained an Activity/Toxicity Factor (Activi-Tox) profile for each product combination from Objective 1 utilizing formulas 1-4. The formulas utilize data from the assays to quantify the activity and/or toxicity of the product relative to a berberine reference standard and then determine a level of berberine in the product which produces a desired level of biological activity.

Table 17 below illustrates how the data from each assay would be complied and used to select the plant part or combination of parts which provides the highest overall rating for activity vs. toxicity. The data will be grouped according to assay and a single average factor determined for each group. For example, data from the four pathogenic bacteria are combined to produce an average antimicrobial activity factor of 2.0 for Sub-Lot B4. All others are similarly grouped and averaged. These averages are then combined and averaged to result in a single Activity Factor and a single Toxicity Factor for each product. The Activity Factor is then divided by the Toxicity Factor in order to arrive at a Activi-Tox rating for each product. An Activi-Tox rating of 1 means the product is equal in overall activity and toxicity to the berberine reference standard. A rating of greater than 1 means the product is overall more active and/or less toxic than the standard and a rating of less than 1 means the product is less active and/or more toxic than the standard. An additional scenario besides the one given would be for the overall activity factor to indicate 5 times the activity of the standard but the toxicity factor is 10 times greater resulting in a an overall rating of 0.5. The Activi-Tox rating is therefore a measure of the amount of synergistic and/or additive toxicity compared to the amount of synergistic and/or additive activity and indicates whether any increases in activity are accompanied by disproportionate levels of toxicity.

Production follows the same procedure as previously described up to the point where the solvent mixture from each of the three extractions are blended into a single batch and before standardization of alkaloid content step.

Antimicrobial Activity Determination

TABLE 17

Data is illustrative of potential results

| Activity Assay | Activity Factor | Toxicity Factor | Toxicity Assay |
|---|---|---|---|
| Antimicrobial | | | Antimicrobial |
| E. Coli | 0.5 | .75 | L. acidolphulis |
| Staph. | 3.0 | | |

TABLE 17-continued

Data is illustrative of potential results

| Activity Assay | Activity Factor | Toxicity Factor | Toxicity Assay |
|---|---|---|---|
| *Camplyobactor* | 2.5 | | |
| *Helicobactor* | 2.0 | | |
| *Shigella* | 2.0 | | |
| Average Antiproliferative | 2.00 | .75 | Average Antiproliferative |
| AGS | 1.5 | 1.0 | Normal Cells |
| CaCo-2 | 1.5 | | |
| Average Antiinflammatory | 1.5 | 1.0 | Average Inflammatory |
| COX-II Inhibition | 1.0 | 1.5 | TNF-α |
| | | 1.0 | sICAM-1 |
| Average | 1.0 | 1.25 | Average Mutagenicity |
| | | 1.0 | *Salmonella* |
| Average of all Activity Assays | 1.5 | 1.25 | Average of all Toxicity Assays |
| Activ-Tox Rating | | 1.2 | | a. Minimum Inhibitory Concentration (MIC) of Goldenseal Extract Preparations Against Selected Human and Animal Pathogens Minimum inhibition concentration (MIC) will be tested in appropriate liquid media in 96-well microtiter plates. Each well contains 5×10$^5$ CFU/ml of test bacteria, serially diluted extracts and medium. In some cases when chemical solvents are used, it will be tested simultaneously with the test compounds to ensure the absence of antimicrobial activity. Triplicate samples are to be performed. All plates will be incubated at 37° C. and growth estimated spectrophotometrically (660 nm) after 48 hr using a microplate reader (molecular device, Vmax kinetics, Menlo Park, Calif.). The MIC for each test bacteria is defined as the minimum concentration of test compound limiting turbidity to <0.05 absorbance at 660 nm.

b. Minimum Bactericidal Concentration of Goldenseal Extract Preparations

Test bacteria will be exposed to goldenseal extract at MIC, 2× MIC, and 5× MIC concentration. After 10 min at 37° C., the treated bacterial (or fungal) culture will be diluted and viable colony counts determined. The ability of goldenseal extract in killing test organisms will be elucidated. The concentration capable of reducing 99.99% viable organism will be noted as MBC.

Antimicrobial Activity of *Hydrastis canadensis* and/or its Isolated Alkaloid Berberine: Methanol extracts of the rhizomes of *Sanguinaria canadensis*, and the roots and rhizomes of *Hydrastis canadensis*, two plants used traditionally for the treatment of gastrointestinal ailments, were screened for in vitro antibacterial activity against 15 strains of *Helicobacter pylori*. The crude methanol extract of *H. canadensis* rhizomes was very active, with an MIC50 of 12.5 microg/ml. Two isoquinoline alkaloids, berberine and beta-hydrastine, were identified as the active constituents, and having an MIC50 of 12.5 and 100.0 microg/ml, respectively (Mahady, 2003), note, the crude extract was equal in activity to the isolated berberine. Antimicrobial constituents from *Hydrastis canadensis* were tested against the oral pathogens *Streptococcus mutans* and *Fusobacterium nucleatum*. Berberine was demonstrated to be the primary compound responsible for the reported strong activity of the crude extract. The data produced by this study was reported to support the use of *Hydrastis canadensis* in oral care products (Hwang, 2003). The antibacterial activity of *Hydrastis canadensis* L. extract and its isolated major alkaloids (berberine, beta-hydrastine, canadine and canadaline) was evaluated against 5 strains of microorganism: *Staphylococcus aureus* (ATCC 25 993 and ATCC 6538P), *Streptococcus sanguis* (ATCC 10 556), *Escherichia coli* (ATCC 25 922), *Pseudomonas aeruginosa* (ATCC 27 853). The results provide a rational basis for the traditional antibacterial use of *Hydrastis canadensis* (Scazzocchio, 2001). A 1998 study conducted at Iowa State University entitled Botanicals for Pigs—Goldenseal compared goldenseal=s use as a natural antimicrobial agent in nursery pigs with Mecadox. The study reported that growth of the pigs on a 1% goldenseal diet were often not statistically different from the Mecadox controls.

Berberine sulfate has been shown to possess growth inhibitory activity against *Giardia lamblia, Trichomonas vaginalis*, and *Entamoeba histolytica* in axenic culture (Kaneda, 1991). It was observed the crude extract was more effective than the salt. The greater inhibitory activity of the crude extract may be due to the cumulative contributions of berberine along with other alkaloids and pharmacologically active constituents (Kaneda, 1990).

Berberine has been the subject of two human studies regarding intestinal parasites. Choudhry et al reported on 40 children (ages 1-10 years) infected with *Giardia*, who received either B-vitamin syrup (which they termed "a placebo"), berberine (5 mg/kg/day) or metronidazole (10 mg/kg/day). The substances were administered in three divided doses for 6 days. Following the placebo, 15% of the subjects became symptom-free and 25% demonstrated no *Giardia* in the stool. After taking berberine, 48% became asymptomatic and 68% were *Giardia*-free upon stool analysis. All of those receiving metronidazole showed no *Giardia* remaining, but only 33% had resolution of symptoms (Choudhry, 1972).

In another study, a total of 137 children (ages 5 months to 14 yr, mean age 5 yr) with documented Giardiasis were given either 5 mg/kg/day or 10 mg/kg/day of berberine in divided doses, for a period of either 5 or 10 days. They were then compared with 242 subjects placed on conventional therapy, including 88 who received metronidazole (20 mg/kg/day for 5-7 days). Ninety percent of those receiving berberine (10 mg/kg/day for 10 days) had negative stool specimens after 10 days, and 83% remained negative one month later, which compared favorably with those treated with metronidazole (95% and 90%, respectively). The author concludes by citing berberine's "convenience of administration and freedom from unpleasant side effects." (Gupte, 1975)

Berberine containing plants have been shown to produce substances which, by themselves, are completely without antimicrobial activity however, when used in conjunction with berberine, enhanced the activity of berberine by as much as 2,500 times (Stermitz, 2000, Tegos, 2002). An example of this phenomenon is presented by Hwang (2003). This report revealed a Minimum Inhibitory Concentration level for berberine, isolated from *Hydrastis*, against *Streptococcus mutans* of 125 μg/ml. All other fractions exhibited either no or very weak activity. The next closest compound was the crude extract at 250 μg/ml, 50% of the activity of the isolated berberine yet it only contained 0.02% berberine or 1/5000$^{th}$ the concentration of the isolated berberine. The exact mechanisms by which this whole extract synergy is accomplished are yet to be fully described. However, Stermitz (2000) reported that some berberine producing plants also produce compounds which, though inactive themselves, greatly enhance the activity of the berberine. These compounds were identified as multi-drug resistant (MDR) efflux pump inhibitors.

It is evident that the level of berberine alone was not the primary factor responsible for the activity of the crude extract in the above study. The fact that no other fraction or combination of active fractions were identified which could account for the increased activity of the crude extract indicates that MDR inhibitors and/or other synergistic compounds exist in *Hydrastis* and therefore that standardization to a specific level of alkaloids alone, as is current industry practice with *Hydrastis*, will never be an accurate representation of its activity. The process described in this application quantifies the effect of these compounds and uses that data to determine a level of berberine in each individual lot of *Hydrastis* products which will produce repeatable bioactivity.

{Anti-Proliferative Activities of Berberine: The relationship between the inhibited growth (cytotoxic activity) of berberine and apoptotic pathway with its molecular mechanism of action was investigated in Lin, (2006) using human gastric carcinoma SNU-5 cells. For SNU-5 cell line, the IC50 was found to be 48 micromol/L of berberine. In SNU-5 cells treated with 25-200 micromol/L berberine, G2/M cell cycle arrest was observed which was associated with a marked increment of the expression of p53, Wee1 and CDk1 proteins and decreased cyclin B. A concentration-dependent decrease of cells in G0/G1 phase and an increase in G2/M phase were detected. In addition, apoptosis detected as sub-G0 cell population in cell cycle measurement was proved in 25-200 micromol/L berberine-treated cells by monitoring the apoptotic pathway. Apoptosis was identified by sub-G0 cell population, and upregulation of Bax, downregulation of Bcl-2, release of $Ca2+$, decreased the mitochondrial membrane potential and then led to the release of mitochondrial cytochrome C into the cytoplasm and caused the activation of caspase-3, and finally led to the occurrence of apoptosis. In addition, berberine exhibited cytototoxic activity against two human cancer cell lines, HT-1080 (human fibrosarcoma) and SNU-638 (human stomach adenocarcinoma), with IC50 values of 3.2 and 3.4 microg/mL, respectively (Kim, 2005).

Berberine was also tested against human tumour HeLa and murine leukemia L1210 cell lines. For both cell lines the IC(50) was found to be less than 4 microg mL(−1), a limit put forward by the National Cancer Institute (NCI) for classification of the compound as a potential anticancer drug. In L1210 cells treated with 10-50 microg mL(−1) berberine, G(0)/G(1) cell cycle arrest was observed. Furthermore, a concentration-dependent decrease of cells in S phase and increase in G(2)/M phase was detected. In addition, apoptosis detected as sub-G(0) cell population in cell cycle measurement was proved in 25-100 microg mL(−1) berberine-treated cells by monitoring the apoptotic DNA fragmentation using agarose gel electrophoresis (Jantova, 2003).

This study was later confirmed by Kettman, 2004. The anti-cancer activity of berberine against a variety of cancer cell lines was extended to human uterus HeLa and murine leukemia L1210 cell lines. Cytotoxicity was measured using in vitro techniques and cell morphology changes were examined by light microscopy in both cytostatic and cytocidal concentration ranges. The IC50 was found to be less than 4 microg/ml. The microscopy examination indicated that at cytocidal concentrations the HeLa and L120 cells died apoptotically. The comparative analysis revealed that berberine belongs to the camptothecin family of drugs characterized by the ability to induce DNA topoisomerase poisoning and hence apoptotic cell death. Although the cytotoxic potency of berberine was found to be several orders of magnitude lower compared to camptothecin, its significance may increase in future in view of the lack of unwanted side effects characteristic for camptothecin compounds currently in clinical use for treatment of cancer.

Berberine acted cytotoxically in vitro on tumor cell line B16. Its anticancer activity in vivo was studied with the transplanted B16 line in the range of doses from 1 mg/kg to 10 mg/kg. A significant reduction of tumor volume was observed on day 16 at doses of 5 and 10 mg/kg (Letasovia, 2005).

The enzyme cyclooxygenase-2 (COX-2) is abundantly expressed in colon cancer cells and plays a key role in colon tumorigenesis. Compounds inhibiting COX-2 transcriptional activity have therefore potentially a chemopreventive property against colon tumor formation. An assay method for estimating COX-2 transcriptional activity in human colon cancer cells was established using a beta-galactosidase reporter gene system, and examination was made of various medicinal herbs and their ingredients for an inhibitory effect on COX-2 transcriptional activity. They found that berberine effectively inhibits COX-2 transcriptional activity in colon cancer cells in a dose- and time-dependent manner at concentrations higher than 0.3 microM. The present findings may further explain the mechanism of anti-inflammatory and anti-tumor promoting effects of berberine (Fukuda, 1999).

Inoue (2005) reported that berberine iodide and acetoneberberine showed higher cytotoxicity against five human oral squamous cell carcinoma and one human promyelocytic leukemia cell lines, than against normal human oral tissue-derived cells and concluded that "The present study demonstrated the tumor-specific cytotoxicity and apoptosis-inducing activity of berberines, suggesting their possible anti-tumor potential". Tumor specific activity was also indicated in Hwang, (2005). This study demonstrated that berberine exhibited significant cytotoxicity in hepatoma HepG2 cells but is ineffective in Chang (normal) liver cells. Yount, (2004) indicated that berberine sensitizes human glioma cells, but not normal glial cells, to ionizing radiation in vitro. Iizuka (2003) reported that the crude extract of "Coptidis rhizoma killed tumor cells more effectively than purified berberine when normalized to the level of berberine present in the herb".

Effect of Berberine on Cholesterol Level

Previous studies identified berberine (BBR) as a unique cholesterol-lowering drug that upregulates hepatic low density lipoprotein receptor (LDLR) expression through a mechanism of mRNA stabilization. Abidi, 2006 demonstrated that the crude root extract of goldenseal, *Hydrastis canadensis*, is highly effective in upregulation of liver LDLR expression in HepG2 cells and in reducing plasma cholesterol and low density lipoprotein cholesterol (LDL-c) in hyperlipidemic hamsters, with greater activities than the pure compound BBR. Through bioassay-driven semipurifications, it was demonstrated that the higher potency of goldenseal is achieved through concerted actions of multiple bioactive compounds in addition to BBR. Canadine (CND) and two other constituents of goldenseal were identified as new upregulators of LDLR expression. It was further shown that the activity of BBR on LDLR expression is attenuated by multiple drug resistance-1 (MDR1)-mediated efflux from liver cells, whereas CND is resistant to MDR1. This finding defines a molecular mechanism for the higher activity of CND than BBR. Substantial evidence was produced to show that goldenseal contains natural MDR1 antagonist(s) that accentuate the upregulatory effect of BBR on LDLR mRNA expression. These new findings identified goldenseal as a natural LDL-c-lowering agent and provide a molecular basis for the mechanisms of action (Abidi, 2006). An earlier study demonstrated that the BBR-induced stabilization of LDLR mRNA is mediated by the ERK signaling pathway through interactions of cis-regulatory sequences of 3'UTR and mRNA binding proteins that are downstream effectors of this signaling cascade (Abidi, 2005).

In order to determine whether this upregulatory effect on LDLR mRNA was produced by SHF *Hydrastis*, SHF *Hydrastis* root/rhizome and leaf/stem extracts were analyzed utilizing the bioassays and reference materials by the authors of Abidi, 2006. SHF extracts, both alone and in combination were compared to Lot # 9, pure berberine and the control compound from the above studies. The results of those studies are presented below.

At a concentration of 1 ml/mg Lot # 9, SHF leaf/stem, and SHF root/rhizome produced an increase in LDLR mRNA that was roughly equivalent even though the level of berberine was 7.23, 0.52, and 1.30 mg/ml respectively. SHF root/rhizome indicated greater activity with increasing concentrations while SHF leaf/stem indicated a downregulatory effect with increasing concentrations. This downregulatory effect was also evident in the combination studies where at equal concentrations, 2.5 mg/ml the upregulatory effect of the root/rhizome was entirely mitigated.

Treatment of hyperlipidemic hamsters with berberine decreased plasma LDL cholesterol and strongly reduced fat storage in the liver. These findings indicate that berberine, in addition to upregulating the LDLR, inhibits lipid synthesis in human hepatocytes through the activation of AMPK (Brusq, 2006).

Oral administration of Berberine (BBR) in 32 hypercholesterolemic patients for 3 months reduced serum cholesterol by 29%, triglycerides by 35% and LDL-cholesterol by 25%. Treatment of hyperlipidemic hamsters with BBR reduced serum cholesterol by 40% and LDL-cholesterol by 42%, with a 3.5-fold increase in hepatic LDLR mRNA and a 2.6-fold increase in hepatic LDLR protein. Using human hepatoma cells, it was shown that BBR upregulates LDLR expression independent of sterol regulatory element binding proteins, but dependent on ERK activation. BBR elevates LDLR expression through a post-transcriptional mechanism that stabilizes the mRNA. Using a heterologous system with luciferase as a reporter, we further identify the 5' proximal section of the LDLR mRNA 3' untranslated region responsible for the regulatory effect of BBR. These findings show BBR as a new hypolipidemic drug with a mechanism of action different from that of statin drugs (Kong, 2004).

This data indicates that standardization to specific levels of chemical markers are not representative of the bioactivity of the product. This invention mitigates this problem by standardizing to biological activity.

Other Pharmacological Activities of Berberine Relevant to Gastrointestinal Disorders: In addition to antimicrobial and antiproliferative activity, berberine has been found to have numerous pharmacological effects that could be beneficial in treating various gastrointestinal disorders including antagonism of the effect of cholera and *E. coli* heat stable enterotoxin (Sack, 1982), delay of small intestine transit time (Eaker, 1989), inhibition of intestinal secretions (Zhu, 1983), significantly inhibit spontaneous peristalsis in the intestine (Birdsall, 1997), inhibition of smooth muscle contraction (Tai, 1981), potent inflammation inhibitory activity (Yesilada, 2002), inhibition of cyclooxygenase-2 (COX-2) transcriptional activity in a dose and time dependent manner (Fukuda, 1999), and inhibition of I1-8 production in rectal mucosa in rats (Zhou, 2000). Berberine was also found to significantly protect gastric mucosa from damage by ethanol (Pan, 2005). Another desirable characteristic of an effective product for gastrointestinal disorders would be slow absorption through the intestine allowing the active principals to remain in contact with the affected surfaces as long as possible. This characteristic of berberine was demonstrated by the report of Pan et al (2003) which found berberine to be hardly absorbed in the intestine (less than 5% in 2.5 hrs). Berberine is considered to be a non-antibiotic, anti-diarrheal drug. Baird, (1997) reported that there is much in common between the anti-diarrheal actions of loperamide and berberine in terms of their pharmacokinetics, an anti-motility action on intestinal smooth muscle and an anti-secretory effect on intestinal epithelia. Since berberine has been shown to be selective in its antimicrobial activity through the demonstration of weak or no inhibition of several "friendly" bacteria including, *Bifidobacterium adolescentis, Lactobacillus acidophilus*, and *Lactobacillus casei* (Chae, 1999), the above studies provide support for future testing of *Hydrastis* products in cases of bacterial diarrhea and other intestinal tract disorders such as ulcers and IBS.

Antimicrobial Characteristics of Goldenseal: Antimicrobial activities of SHF NOP certified *Hydrastis* were evaluated and compared to that of pure chemical berberine sulfate and berberine chloride. The MIC and MBC of *Hydrastis* water extracts, 100% methanol extracts, and 60% methanol extracts against *E. coli* strain ORN178 were measured. The synergistic effects of berberine with the known MDR pump inhibitor (reserpine and orthovanadate) as well as *Hydrastis* root extracts with leaf extracts were also determined. Please refer to the Materials and Methods section for detailed protocol. All extracts were lyophilized and reconstituted in $H_2O$.

The MIC and MBC of berberine sulfate with MDR pump inhibitors are listed in Table 13. The MIC of *Hydrastis* using different extraction solvents are listed in Table 14.

TABLE 13

MIC and MBC of Berberine with MDR Pump Inhibitors Reserpine[a] and Orthovanadate[b]

| Sample | MIC (µg/ml berberine) | MBC (µg/ml berberine) |
| --- | --- | --- |
| Berberine - chloride or sulfate | 62.5 | 125 |
| Berberine - chloride or sulfate + 10 µg/ml Reserpine | 31.25 | 31.25 |
| Berberine - chloride or sulfate + 2 mM Orthovanadate | 31.25 | 31.25 |

[a]Reserpine was added to the cells 5 min after addition of berberine sulfate.

[b]Orthovanadate was added to the cells 20 min before the addition of berberine sulfate The measured MIC and MBC of berberine against *E. coli* ORN178 is 62.5 and 125 µg/ml, respectively. The MIC of berberine reduced by half and MBC reduced to ¼ when 10 µg/ml of reserpine or 2 mM of orthovanadate were supplemented. Up to 5000 µg/ml of reserpine or 4 mM of orthovanadate have been determined to be non-inhibitory to *E. coli* ORN178.

TABLE 14

Comparison of MIC of Goldenseal plant powders extracted using different Extraction Solvents

| Sample | Water Extract (µg/ml) | | 100% Methanol Extracts (µg/ml) | | 60% Methanol Extracts (µg/ml) | |
|---|---|---|---|---|---|---|
| | MIC | MBC | MIC | MBC | MIC | MBC |
| Sleepy Hollow Farm Root | 1250 | 1250 | 312.5 | 312.5 | 156 | 312.5 |
| Sleepy Hollow Farm Leaf | 5000 | 5000 | 1250 | 1250 | 2500 | 2500 |

*Hydrastis* root extract using 60% methanol as solvent has lower MIC than the 100% methanol or water extracts. In addition data from our other work indicates a 60% ethanol mixture is the preferred ratio for optimal alkaloid extraction. Therefore we have chosen to use 60% ethanol as the preferred extraction solvent. Leaf extracts have much higher MIC and MBC against *E. coli* ORN178.

TABLE 15

Synergistic Effect of *Hydrastis* Root (60% Methanol) and Leaf (60% Methanol) Extracts

| Extract | Root | Root + Leaf (156 µg/ml) | Root + Leaf (312 µg/ml) | Root + Leaf (625 µg/ml) | Root + Leaf (1250 µg/ml) |
|---|---|---|---|---|---|
| MIC (µg/ml) | 160 | 160 | 80 | 40 | 20 |

When sub-lethal concentration of leaf extract (1250 µg/ml) was added to root extract, the MIC was ⅛ of root extract alone and ⅓ of the berberine chloride. This data indicates that it is possible to increase the activity of the crude root extract to exceed that of the berberine reference standard by varying the proportion of plant parts. A *Hydrastis* product produced from a mixture of approximately 1 part *Hydrastis* root/rhizome to 8 parts *Hydrastis* leaf/stem would be eight times more active than a root/rhizome product alone and three times more active than the standard. Based on this data, a product could have produced that would have exhibited activity roughly equivalent to a berberine reference standard in this particular assay utilizing approximately 3 parts leaf to 1 part root.

Current industry practice is to primarily use the root/rhizome leading to the destruction of the entire plant when it is harvested, there is very little market for *Hydrastis* leaf/stem. This project is innovative in that it challenges this practice through optimal utilization of the whole plant. This would offer many benefits to not only growers through the development of a market for raw material that is currently viewed as waste but also for the environment as it could drastically reduce the need for wild collected root/rhizome. Consumers will benefit from a more reliable product.

Additional preliminary data regarding the potential synergistic activity of *Hydrastis* leaf on two *Staph.* strains SA-1199B and SA-K2068 was developed using *Hydrastis* extracts. SA-1199B over expresses the NorA MDR efflux protein, SA-K2068, exhibits an MDR efflux phenotype conferred by a pump distinct from NorA. Table 16.

TABLE 16

| Antimicrobial Agent | SA 1199B MIC (µg/ml) | SA K2068 MIC (µg/ml) |
|---|---|---|
| Leaf-1 60% MeOH Extract | 2500 | 1250 |
| Ciprofloxacin | 8 | 4 |

TABLE 16-continued

| Antimicrobial Agent | SA 1199B MIC (µg/ml) | SA K2068 MIC (µg/ml) |
|---|---|---|
| Ciprofloxacin | | |
| +1250 µg/mL leaf ext. | <0.5 | — |
| +625 µg/mL leaf ext. | 2 | 0.5 |
| +312.5 µg/mL leaf ext. | 2 | 0.5 |
| +5~20 µg/mL Reserpine | 1 | 0.5 |

The effect of reserpine on Staph. MDR pumps is in line with published literature. These experiments produced significant data indicating that there are potential MDR pump inhibitor(s) in *Hydrastis* leaf extracts and that adjusting the concentration of the crude leaf extract produced variations in the activity of the root/rhizome or other antimicrobial agent. Note that the crude *Hydrastis* leaf extract produced an increase in activity equal to or greater than reserpine, a known MDR pump inhibitor which is considered too toxic for use at the concentrations necessary to achieve the effect.

*Helicobactor pylori* is a causative agent for chronic gastritis, gastric and duodenal ulcers, and some forms of gastric cancer. In 1994, *H. pylori* was the first bacterium to be classified as a Group 1 carcinogen and has been positively linked to the development of gastric and colon cancer. Conventional eradication therapies typically consist of two antibiotics plus either a proton-pump inhibitor or a bismuth compound (triple therapy). Although current antibiotic treatments are effective in treating this pathogen, some strains of *H. pylori* have developed antibiotic resistance and render treatment less effective, highlighting a need for therapeutic alternatives. *Hydrastis* extract, produced by SHF and containing ca. 0.25% to 0.30% berberine was evaluated for antimicrobial activity against *H. pylori* using a standard disk diffusion method. Our preliminary study demonstrated that *H. pylori* was strongly inhibited by 20 μl *Hydrastis* extract/disk.

| Effect of berberine chloride, *Hydrastis* root or leaf extracts on the growth of ACS cells | | | | | | |
|---|---|---|---|---|---|---|
| | % growth reduction of AGS cells | | | | | |
| Extracts | μl | μl | μl | μl | 6 μl | 0 μl |
| Berberine chloride[a] | .7 | .5 | 3.7 | 2.6 | 2.1 | 4.2 |
| *Hydrastis* root extract | E[b] | E | 2.6 | 4.8 | 1.7 | 1.3 |
| *Hydrastis* leaf extract | E | E | E | .9 | 4.2 | 1.2 |

[a]*Hydrastis* root extract contained the same amount of berberine chloride as the berberine chloride control (500 μg/ml), whereas *Hydrastis* leaf extract contained one fifth of the berberine chloride in control.
[b]NA, no effect.

Human gastric adenocarcinoma (AGS) cells were grown as described below and preliminary data developed regarding the antiproliferative activity of *Hydrastis* extracts and berberine. 20 μl of *Hydrastis* root extract containing 500 μg/ml berberine and a reference solution containing an equivalent amount of berberine chloride exhibited similar levels of activity, indicating that berberine is primarily responsible for the activity of the root extract. *Hydrastis* leaf extract produced activity slightly less than the control or root extract but contained one fifth of the berberine indicating synergistic and/or additive compounds exist in the leaf.

Another study at Clemson examined the anti-tumor properties of berberine when combined with pump inhibitory characteristics of leaf extracts from *Hydrastis*. This combination inhibited proliferation of both CaCo2, a colon epithelial cell line, and McF7, a breast epithelial cell line. *Hydrastis*, a common herb, has been shown to possess both anti-tumor properties in its active ingredient berberine, and pump inhibitory characteristics in its leaf. Anti-tumor properties block uncontrolled growth, while pump inhibitory properties aid in lowering the dosage of drugs needed to treat the patient.

MTS assay was used to measure cell proliferation. Cell proliferation of McF7 was reduced to 45% of the control when treated with 2% of berberine. *Hydrastis* leaf extract, at a concentration of 2%, exhibited little or no anti-proliferation activity against McF7. However, a synergetic effect was observed when combining 0.5% berberine with 1.5% leaf extract. Proliferation of McF7 was reduced to 59% compared to the untreated cells.

Similar result has been observed with CaCo2 cell line. When treated with 0.5% berberine, a 75% cell proliferation was observed while 0.5% of leaf extract along showed no effect. The combination of 0.5% berberine and 0.5% leaf extract resulted in a 48% cell proliferation rate suggested a synergistic effect of the two compounds on this cell line.

In conclusion, cell proliferation of both colon and breast cell lines were inhibited by berberine. Leaf extract, while limited in anti-tumor activity by itself, potentiated the activity of berberine possibly through inhibiting the P-glycoprotein pump activity of tumor cells.

Antineoplastic—Cancer Cell Cultures. This assay measures the ability of *Hydrastis* to stimulate or arrest metabolic activity of tumor cells. Human gastric adenocarcinoma (AGS), $CaCO_2$ colon cancer cells and normal colon epithelial tissue (ATCC) will be grown in Petri plates on Dulbecco's Modified Eagle Medium (DME) with 4 mM L-glutamine, 4.5 g/l glucose and 10% fetal bovine serum. CRL 7368 Breast Cancer cells and CRL 7367 Fibroblast control cells will be grown in Petri plates on DME with 4 mM L-glutamine, 4.5 g/l glucose, 1.5 g/l sodium bicarbonate and 10% fetal bovine serum. A 95% confluent layer of healthy cells will be divided as follows: surface media will be poured from the plates so that the cells are not dislodged. Ten milliliters of sterile phosphate-buffered saline (PBS) will be added to the plates to rinse the cell layer and then discarded. The PBS rinsing will be repeated three times followed by the addition of 4 ml trypsin-EDTA and incubation at 37° C. for approximately 5 min. Cellular release by the trypsin is indicated when the cell layer moves when the plate is tilted. Dislodged cells will be added to 15 ml sterile tubes containing 1 ml calf serum. The cell suspension will be centrifuged at 1600 rpm for 5 min, the supernatant decanted. The cellular pellet is suspended in 5 ml of medium by mixing. A cell suspension aliquot (0.1 ml) is added to 0.9 ml of 0.4% Trypan Blue and mixed. Cell counts will be made using a hemocytometer charged with the cell suspension. Aliquots of the cell suspension (based on cell count) will be added to Petri plates, then 15 ml of media will be added and the plates incubated at 37° C. in a $CO_2$ incubator. Cells will be checked daily for contamination and morphology. Media will be replaced every 2 to 3 days with fresh medium.

The Cell Titer 96® $AQ_{ueous}$ Non-radioactive Cell proliferation Assay manufactured by Promega, is a colorimetric method used to measure dehydrogenase activity found in metabolically active cells. The MTS is reduced to formazan in the presence of metabolically active cells and the absorbance of formazan is measured spectrophotometrically. Two days post subculture, cells will be rinsed twice with respective media, harvested, and the cell concentration adjusted to $1 \times 10^5$ cells/ml. Fifty μl of the cell suspension will be added to the individual wells of a 96-well microtiter plate. Each well will contain 50 μl of the test sample (extract) or standard reference drug. Plates will be incubated for 48 to 72 hr at 37° C. in a $CO_2$ incubator. After incubation, 20 μl of MTS/PMS solution will be added, and the plates incubated for an additional 1 to 4 hr. At the end of the incubation period, absorbance will be recorded at 490 nm.

Cellular Cyclooxygenase and Lipoxygenase Inhibition. Eicosanoids derived from the cyclooxygenase and lipoxygenase pathways contribute to inflammatory and immune responses. These two enzymatic activities are widely accepted within the pharmaceutical and nutraceutical industries as initial screens for anti-inflammatory activities of individual compounds and/or complex mixture of compounds. The testing of an herbal extract can be compared to known anti-inflammatory drugs such as indomethacin. (IC50 of the herbal extract vs the IC50 of indomethacin). In these studies we will determine the effects of *Hydrastis* extracts on the production of prostaglandins and leukotrienes, potent inflammatory mediators derived from arachidonic acid via the cyclooxygenase and lipoxygenase pathways, respectively (Hanada, 2002). Culture supernatants from human peripheral blood mononuclear cells treated with *Hydrastis* extracts will be assayed at various times and various concentrations for prostaglandin $E_2$ and leukotriene $LTB_4$ by ELISA, using commercially available kits from R&D Systems. If prostaglandin $E_2$ and/or leukotriene $LTB_4$ levels are altered following treatment of cells with the goldenseal extracts, we will also assess whether the extracts can alter the production of the mRNA for the enzymes involved in the synthesis of prostaglandin $E_2$ and/or leukotriene $LTB_4$, cyclooxygenase-2 and 5-lipoxygenase, respectively. This will be done by measuring the amount of mRNA for these enzymes by real time PCR. Human peripheral blood mononuclear cells will be treated with goldenseal extracts for various times and total RNA will be extracted using an RNeasy kit (Qiagen Inc.). RNA quality and integrity will be checked by non-denaturing gel electrophoresis. The RNA will then be used to make cDNA using the Omniscript reverse transcription method (Qiagen, Inc.). Real-time PCR reactions will be carried out using a SYBR Green PCR core reagent kit (Applied Biosystems) and primers specific for the cyclooxygenase-2 or 5-lipoxygenase genes. Messenger RNA levels for RPLP0 (ribosomal protein, large, P0) will be measured as an internal standard. The PCR products will be detected using a real-time iCycler IQ detection system (Biorad Laboratories). Primers will be designed using Oligo (Molecular Biology Insights Inc) to cross an exon/exon boundary to minimize the chance that a signal will be from contaminating DNA. To check that genomic DNA is not a problem, real-time PCR will be performed using mock reverse transcription reactions in which the reverse transcriptase is omitted. All real-time PCR reactions will include a melt curve to examine the specificity of PCR product and to ensure that primer-dimer artifacts are not interfering with the measurements. Real-time PCR assays will be carried out in triplicate for each sample and the average value at which the PCR product crosses the threshold (Ct) calculated. The ratio of target gene mRNA expression relative to that of the internal standard mRNA (RPLP0) will be calculated using the following equation where E=the efficiency of real-time PCR amplification for the appropriate gene.

$$\text{ratio} = \frac{(E_{target})^{\Delta Cttarget(control-treated)}}{(E_{RPLP0})^{\Delta CtRPLP0(control-treated)}}$$

To calculate the efficiency 10-fold serial dilutions of cyclooxygenase-2 DNA, 5-lipoxygenase DNA or RPLP0 DNA will be subjected to real-time PCR and the efficiency calculated from a plot of Ct versus the logarithm of the concentration of the DNA using the equation $E=10^{-1/slope}$.

Alternative Method of Manipulating the Concentration Level the Pharmacologically Active Compounds in Goldenseal Extracts An alternative method of arriving at a desired concentration level of pharmacologically active compounds in goldenseal extracts begins with raw goldenseal cultivated using the preferred method, selectively harvested based or whether the plants are reproductive or sterile, then separating the various parts of each. The various plant parts from the reproductive plants and the various plant parts from the sterile plants are individually processed by drying, grinding, and extraction as previously described. Before the individual extracts are combined, samples are taken from each and quantitatively analyzed for berberine/hydrastine content using one of the analytical methods previously described. These extracts will contain various ratios of berberine/hydrastine depending upon which part is extracted and the stage of extraction, first, second, or third. These extracts are then combined in calculated amounts to produce the desired levels and ratios of berberine/hydrastine or further concentrated and standardized using the preferred method.

Second Alternative Method of Manipulating the Concentration Level the Pharmacologically Active Compounds in Goldenseal Extracts A second alternative method of arriving at a desired concentration level of pharmacologically active compounds in goldenseal extracts begins with raw goldenseal cultivated using the preferred method, selectively harvested based or whether the plants are reproductive or sterile, then separating the various parts of each. The various plant parts from the reproductive plants and the various plant parts from the sterile plants are individually processed by drying and grinding as previously described. The resulting powders are individually quantitatively analyzed for berberine/hydrastine content using one of the analytical methods previously described. The powders are then blended in calculated amounts to produce a composition to be used for extraction which has desired ratios and levels of berberine/hydrastine.

This pre-standardized powder is then extracted using the previously described method. The compositions from the 3 extraction stages are then either combined, analyzed and standardized to a desired level and/or ratio of berberine/hydrastine as described in the preferred method or individually analyzed, then combined to produce a desired level and/or ratio of berberine/hydrastine as described in the first alternative method.

The methods of the present invention are expected to have most widespread application in differentiating, improving and achieving reproducibility or standardization of herbal processing techniques, particularly extraction of pharmacologically active mixtures from plant sources and in obtaining plant extracts of reliable pharmacological activity. The reproducibility and standardization procedures of the invention involve the use of a combination of pharmacological and chemical analysis of the isolated products, typically obtained in extraction procedures.

The pharmacological tests performed on the process products, preferably plant extracts, most preferably the plant extract obtained from goldenseal, may be in the form of in vitro and/or in vivo pharmacological tests. In the present invention it is preferred that at least two in vitro and at least two in vivo pharmacological tests be used. These tests are generally correlated with a changed biological state of a living organism. This may take the form of either an enhanced condition of the organism or an effective treatment of a medical condition in a patient.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks and other references (e.g., journal articles) that contain definitions and methods and means for carrying out basic techniques, encompassed by the present invention.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

Abidi P, Chen W, Kraemer F B, Li H, Liu J, 2006. *The medicinal plant goldenseal is a natural LDL-lowering agent with multiple bioactive components and new action mechanisms* J Lipid Res. October; 47(10):2134-47.

Abidi P, Zhou Y, Jiang J D, Liu J, 2005. *Extracellular signal-regulated kinase-dependent stabilization of hepatic low-* density lipoprotein receptor mRNA by herbal medicine berberine Arterioscler Thromb Vasc Biol. October; 25(10):2170-6.

Abourashed, E. A., and Khan, I. A., 2001. *High-performance liquid chromatography determination of hydrastine and berberine in dietary supplements containing goldenseal.* J Pharm Sci 90(7):817-22

American Herbal Products Association (AHPA) 2006. *Tonnage Survey of Select North American Wild-Harvested Plants, 2002-2003.* Silver Spring (MD): American Herbal Products Association;

Amin A H, Subbaiah T V, Abbasi K M, 1969. *Berberine sulfate: antimicrobial activity, bioassay, and mode of action.* Can J Microbiol 15:1067-1076.

Anis K V, Rajeshkumar N V, Kuttan R., 2001. *Inhibition of chemical carcinogenesis by berberine in rats and mice.* J Pharm Pharmacol. May; 53(5):763-8.

Asai M, Iwata N, Yoshikawa A, Aizaki Y, Ishiura S, Saido T C, Maruyama K, 2007. *Berberine alters the processing of Alzheimer's amyloid precursor protein to decrease Abeta secretion* Biochem Biophys Res Commun. January 12; 352(2):498-502.

Baird, A. W., C. T. Taylor, and D. J. Brayden. 1997. *Non-antibiotic Anti-diarrheal Drugs: Factors Affecting Oral Bioavailability of Berberine and Loperimide in Intestinal Tissue.* Adv. Drug Delivery Rev. 23:111-120.

Bennish, Michael, 2004. *Micronutrients and Enteric Infection in African Children.* NIH CRISP database, accessed on the world wide web Aug. 2, 2004.

Birdsall T C, Kelly G S, 1997. *Berberine: Therapeutic potential of an alkaloid found in several medicinal plants.* Altern. Med. Rev. 2:94-103.

Brusq J M, Ancellin N, Grondin P, Guillard R, Martin S, Saintillan Y, Issandou M., 2006. *Inhibition of lipid synthesis through activation of AMP kinase: an additional mechanism for the hypolipidemic effects of berberine.* J Lipid Res. June; 47(6):1281-8.

Bustanji Y, Taha M O, Yousef A M, Al-Bakri A G, 2006. *Berberine potently inhibits protein tyrosine phosphatase 1B: investigation by docking simulation and experimental validation.* J Enzyme Inhib Med. Chem. April; 21(2):163-71.

Chae S H, Jeong I H, Choi D H, Oh J W, Ahn, Y J, 1999. *Growth-inhibiting effects of Coptis japonica root-derived isoquinoline alkaloids on human intestinal bacteria.* J. Agric. Food Chem. March; 47(3):934-8.

Chatterjee P, Franklin M R, 2003. *Human cytochrome p450 inhibition and metabolic-intermediate complex formation by goldenseal extract and its methylenedioxyphenyl components.* Drug Metab Dispos. November; 31(11):1391-7.

Cheng Z, Pang T, Gu M, Gao A H, Xie C M, Li J Y, Nan F J, Li J, 2006. *Berberine-stimulated glucose uptake in L6 myotubes involves both AMPK and p38 MAPK.* Biochim Biophys Acta. November; 1760(11):1682-9.

Cho K M, Yoo I D, Kim W G, 2006. *8-hydroxydihydrochelerythrine and 8-hydroxydihydrosanguinarine with a potent acetylcholinesterase inhibitory activity from Chelidonium majus L.* Biol Pharm Bull. November; 29(11):2317-20.

Cho B J, Im E K, Kwon J H, Lee K H, Shin H J, Oh J, Kang S M, Chung J H, Jang Y., 2005. *Berberine inhibits the production of lysophosphatidylcholine-induced reactive oxygen species and the ERK1/2 pathway in vascular smooth muscle cells.* Mol. Cells. December 31; 20(3):429-34.

Choudhry V P, Sabir M, Bhide V N, 1972. *Berberine in giardiasis.* Indian Pediat 9:143-146.

Cui H S, Hayasaka S, Zhang X Y, Hayasaka Y, Chi Z L, Zheng L S, 2006a. *Effect of berberine on interleukin 8 and monocyte chemotactic protein 1 expression in a human retinal pigment epithelial cell line.* Ophthalmic Res.; 38(3):149-57.

Cui H S, Hayasaka S, Zheng L S, Hayasaka Y, Zhang X Y, Chi Z L, 2006b. *Effect of Berberine on Monocyte Chemotactic Protein-1 and Cytokine-Induced Neutrophil Chemoattractant-1 Expression in Rat Lipopolysaccharide-Induced Uveitis.* Ophthalmic Res. December 11; 39(1):32-39

Davis, J. M., 2000. *Commercial Cultivation of Goldenseal* Horticultural Information Leaflet # 131 N.C. Coop. Extension Service N.C. State University Eaker E Y, Sninsky C A, 1989. *Effect of berberine on myoelectric activity and transit of the small intestine in rats.* Gastroenterology 96(6):1506-13

Edwards D J, Draper E J, 2003, *Variations in alkaloid content of herbal products containing goldenseal.* J Am Pharm Assoc (Wash DC) May-June; 43(3):419-23.

Food and Drug Administration (FDA). 1995. *Bacteriological Analytical Manual,* 8th Edition, AOAC International, Gaithersburg, Md.

FDA, 1999. *Economic Characterization of the Dietary Supplement Industry Final Report,* Section 5, U.S. Food and Drug Administration, Center for Food Safety and Applied Nutrition. Accessed on the World Wide Web Jul. 24, 2002 at http://vm.cfsan.fda.gov/~comm/ds-econ5.html Fleckenstein, J M, 2004. *Pathogenesis of ETEC Infections.* NIH CRISP database, accessed on the world wide web Aug. 2, 2004.

Foster, Steven and Duke, James, A. 1990 *A Field Guide to Medicinal Plants: Eastern and Central North America.* Houghton Mifflin Co.

Frasa, H., B. Benaissa-Trouw, L. Tavares, K. van Kessel, M. Poppelier, K. Kraaijeveld, and J. Verhoef. 1996. *Enhanced protection by use of a combination of anticapsule and antilipopolysaccharide monoclonal antibodies against lethal Escherichia coli O18K5 infection of mice.* Infect. Immun. 64: 775-781.

Fukuda K, Hibiya Y, Mutoh M, Koshiji M, Akao S, Fujiwara H. 1999. *Inhibition by berberine of cyclooxygenase-2 transcriptional activity in human colon cancer cells.* J Ethnopharmacol. 66(2):227-233

Gentry E J, Jampani H B, Keshavarz-Shokri A, Morton M D, Velde D V, Telikepalli H, Mitscher L A, Shawar R, Humble, D, Baker W., 1998. *Antitubercular natural products: berberine from the roots of commercial Hydrastis canadensis powder. Isolation of inactive 8-oxotetrahydrothalifendine, canadine, beta-hydrastine, and two new quinic acid esters, hycandinic acid esters-1 and -2.* J Nat. Prod. October; 61(10):1187-93.

Govindan, Meledath and Geetha Govindan, 2000. *A convenient method for the determination of the quality of goldenseal.* Fitoterapia 71:232-235.

Gupte S., 1975. *Use of berberine in treatment of giardiasis.* Am J Dis Child 129:866.

Hamon, N. W. 1990. *Goldenseal.* Can. Pharm. J. 123(11): 508-510.

Han Y, Lee J H, 2005. *Berberine synergy with amphotericin B against disseminated candidiasis in mice.* Biol Pharm Bull. March; 28(3):541-4.

HerbalGram, 2003, American Botanical Council, http://www.herbalgram.org/wholefoodsmarket/herbalgram/articleview.asp?a=66

Hong Y, Hui S S, Chan B T, Hou J, 2003. *Effect of berberine on catecholamine levels in rats with experimental cardiac hypertrophy.* Life Sci. April 18; 72(22):2499-507.

Hong Y, Hui S C, Chan T Y, Hou J Y, 2002. *Effect of berberine on regression of pressure-overload induced cardiac hypertrophy in rats.* Am J Chin Med.; 30(4):589-99.

Hsiang C Y, Wu S L, Cheng S E, Ho T Y, 2005. *Acetaldehyde-induced interleukin-1 beta and tumor necrosis factor-alpha production is inhibited by berberine through nuclear factor-kappaB signaling pathway in HepG2 cells.* J Biomed Sci. October; 12(5):791-801.

Huang C, Zhang Y, Gong Z, Sheng X, Li Z, Zhang W, Qin Y, 2006. *Berberine inhibits 3T3-L1 adipocyte differentiation through the PPARgamma pathway.* Biochem Biophys Res Commun. September 22; 348(2):571-8.

Hwang J M, Kuo H C, Tseng T H, Liu J Y, Chu C Y, 2005. *Berberine induces apoptosis through a mitochondria/caspases pathway in human hepatoma cells.* Arch Toxicol. September 28; 1-12

Hwang J M, Wang C J, Chou F P, Tseng T H, Hsieh Y S, Lin W L, Chu C Y, 2002. *Inhibitory effect of berberine on tert-butyl hydroperoxide-induced oxidative damage in rat liver.* Arch Toxicol. November; 76(11):664-70.

Hwang Bang Yeon, Sara K. Roberts, Lucas R. Chadwick, Christine D. Wu, A. Douglas Kinghorn, 2003. *Antimicrobial Constituents from Goldenseal (the Rhizomes of Hydrastis canadensis) against Selected Oral Pathogens.* Planta Medica; 69; 623-627

Inoue K, Kulsum U, Chowdhury S A, Fujisawa S, Ishihara M, Yokoe I, Sakagami H, 2005. *Tumor-specific cytotoxicity and apoptosis-inducing activity of berberines.* Anticancer Res. November-December; 25(6B):4053-9

Issat T, Jakobisiak M, Golab J., 2006. *Berberine, a natural cholesterol reducing product, exerts antitumor cytostatic/cytotoxic effects independently from the mevalonate pathway.* Oncol Rep. 2006 December; 16(6):1273-1276.

Iwasa K., Lee D. U., Kang S. I. and W. Wiegrebe. 1998. *Antimicrobial Activity of 8-Alkyl- and 8-Phenyl-Substituted Berberines and Their 12-Bromo Derivatives* J. Nat. Prod. 61:1150-1153.

Iwu, M. W., A. R. Duncan, and C. O. Okunji. 1999. *New antimicrobials of plant origin.* p. 457B462. In: J. Janick (ed.), Perspectives on new crops and new uses. ASHS Press, Alexandria, Va.

Iizuka N, Oka M, Yamamoto K, Tangoku A, Miyamoto K, Miyamoto T, Uchimura S, Hamamoto Y, Okita K., 2003. *Identification of common or distinct genes related to antitumor activities of a medicinal herb and its major component by oligonucleotide microarray.* Int J Cancer. 2003 Nov. 20; 107(4):666-72.

Jahnke G D, Price C J, Marr M C, Myers C B, George J D, 2006. *Developmental toxicity evaluation of berberine in rats and mice* Birth Defects Res B Dev Reprod Toxicol. June; 77(3): 195-206.

Jantova S, Cipak L, Letasiova S, 2007. *Berberine induces apoptosis through a mitochondrial/caspase pathway in human promonocytic U937 cells.* Toxicol In Vitro. February; 21(1):25-31.

Jantova S, Cipak L, Cemakova M, Kost'alova D., 2003. *Effect of berberine on proliferation, cell cycle and apoptosis in HeLa and L1210 cells.* J Pharm Pharmacol. August; 55(8): 1143-9.

Judge, N. A., H. S. Mason, and A. D. O'Brien. 2004. *Plant Cell-Based Intimin Vaccine Given Orally to Mice Primed with Intimin Reduces Time of Escherichia coli O157:H7 Shedding in Feces.* Infect. Immun. 72: 168-175.

Kahn, I. A., 2004. *Scientific Approaches to Quality Assessment of Botanical Products Conference* Sep. 7-9, 2004 University of Mississippi Kaneda Y, Tanaka T, Saw T, 1990. *Effects of berberine, a plant alkaloid, on the growth of anaerobic protozoa in axenic culture.* Tokai J Exp Clin Med 1990; 15:417-423.

Kaneda Y, Torii M, Tanaka T, Aikawa M., 1991. *In vitro effects of berberine sulphate on the growth and structure of Entamoeba histolytica, Giardia lamblia and Trichomonas vaginalis.* Ann Trop Med Parasitol 85:417-425.

Kang D G, Sohn E J, Kwon E K, Han J H, Oh H, Lee H S, 2002. *Effects of berberine on Angiotensin-converting enzyme and NO/cGMP system in vessels.* Vascul Pharmacol. December; 39(6):281-6.

Kang B Y, Chung S W, Cho D, Kim T S, 2002. *Involvement of p38 mitogen-activated protein kinase in the induction of interleukin-12 p40 production in mouse macrophages by berberine, a benzodioxoloquinolizine alkaloid.* Biochem Pharmacol. May 15; 63(10):1901-10.

Kawashima K, Fujimura Y, Makino T, Kano Y, 2006. *Pharmacological properties of traditional medicine (XXXII): protective effects of hangeshashinto and the combinations of its major constituents on gastric lesions in rats.* Biol Pharm Bull. September; 29(9):1973-5.

Kettmann V, Kosfalova D, Jantova S, Cernakova M, Drimal J. 2004. *In vitro cytotoxicity of berberine against HeLa and L1210 cancer cell lines.* Pharmazie. July; 59(7):548-51.

Kim H R, Min H Y, Jeong Y H, Lee S K, Lee N S, Seo E K 2005. *Cytotoxic constituents from the whole plant of Corydalis pallida.* Arch Pharm Res. November; 28(11):1224-7

Kim S H, Shin D S, Oh M N, Chung S C, Lee J S, Oh K B, 2004. *Inhibition of the bacterial surface protein anchoring transpeptidase sortase by isoquinoline alkaloids.* Biosci Biotechnol Biochem. February; 68(2):421-4.

Kim T S, Kang B Y, Cho D, Kim S H, 2003. *Induction of interleukin-12 production in mouse macrophages by berberine, a benzodioxoloquinolizine alkaloid, deviates CD4+ T cells from a Th2 to a Th1 response.* Immunology. July; 109(3):407-14.

King C K, Glass R, Bresee J S, Duggan C, 2003. *Managing Acute Gastroenteritis Among Children* National Center for Infectious Diseases MMWR.

Ko B S, Choi S B, Park S K, Jang J S, Kim Y E, Park S, 2005. *Insulin sensitizing and insulinotropic action of berberine from Cortidis rhizoma.* Biol Pharm Bull. August; 28(8): 1431-7.

Kong W, Wei J, Abidi P, Lin M, Inaba S, Li C, Wang Y, Wang Z, Si S, Pan H, Wang S, Wu J, Wang Y, Li Z, Liu J, Jiang J D, 2004. *Berberine is a novel cholesterol-lowering drug working through a unique mechanism distinct from statins.* Nat. Med. December; 10(12):1344-51.

Kuo C L, Chi C W, Liu T Y, 2005. *Modulation of apoptosis by berberine through inhibition of cyclooxygenase-2 and Mcl-1 expression in oral cancer cells.* In Vivo. January-February; 19(1):247-52.

Kuo C L, Chi C W, Liu T Y, 2004. *The anti-inflammatory potential of berberine in vitro and in vivo.* Cancer Lett. January 20; 203(2):127-37.

Kurioka, T. Y. Yunou, and E. Kita. 1998. *Enhancement of Susceptibility to Shiga Toxin-Producing Escherichia coli O157:H7 by Protein Calorie Malnutrition in Mice.* Infect. Immun. 66: 1726-1734.

Lau C W, Yao X Q, Chen Z Y, Ko W H, Huang Y, 2001. *Cardiovascular actions of Berberine.* Cardiovasc Drug Rev. Fall; 19(3):234-44.

Lee Y S, Kim W S, Kim K H, Yoon M J, Cho H J, Shen Y, Ye J M, Lee C H, Oh W K, Kim C T, Hohnen-Behrens C, Gosby A, Kraegen E W, James D E, Kim J B, 2006. *Berberine, a natural plant product, activates AMP-activated protein kinase with beneficial metabolic effects in diabetic and insulin-resistant states*. Diabetes. August; 55(8):2256-64.

Lee S, Lim H J, Park H Y, Lee K S, Park J H, Jang Y, 2006. *Berberine inhibits rat vascular smooth muscle cell proliferation and migration in vitro and improves neointima formation after balloon injury in vivo. Berberine improves neointima formation in a rat model*. Atherosclerosis. May; 186(1):29-37.

Leng S H, Lu F E, Xu L J, 2004. *Therapeutic effects of berberine in impaired glucose tolerance rats and its influence on insulin secretion*. Acta Pharmacol Sin. April; 25(4):496-502.

Letasiova S, Jantova S, Muckova M, Theiszova M, 2005. Antiproliferative activity of berberine in vitro and in vivo. Biomed Pap Med Fac Univ Palacky Olomouc Czech Repub. December; 149(2):461-3

Letasiova S, Jantova S, Cipak L, Muckova M, 2006. *Berberine-antiproliferative activity in vitro and induction of apoptosis/necrosis of the U937 and B16 cells*. Cancer Lett. August 8; 239(2):254-62.

Lee C J, Lee J H, Seok J H, Hur G M, Park Y C, Seol I C, Kim Y H, 2003. *Effects of baicalein, berberine, curcumin and hesperidin on mucin release from airway goblet cells*. Planta Med. June; 69(6):523-6.

Li F, Wang H D, Lu D X, Wang Y P, Qi R B, Fu Y M, Li C J, 2006. *Neutral sulfate berberine modulates cytokine secretion and increases survival in endotoxemic mice*. Acta Pharmacol Sin. September; 27(9):1199-205.

Liang K W, Ting C T, Yin S C, Chen Y T, Lin S J, Liao J K, Hsu S L, 2006. *Berberine suppresses MEK/ERK-dependent Egr-1 signaling pathway and inhibits vascular smooth muscle cell regrowth after in vitro mechanical injury*. Biochem Pharmacol. March 14; 71(6):806-17.

Lin C C, Kao S T, Chen G W, Chung J G, 2005. *Berberine decreased N-acetylation of 2-aminofluorene through inhibition of N-acetyltransferase gene expression in human leukemia HL-60 cells*. Anticancer Res. November-December; 25(6B):4149-55.

Lin S S, Chung J G, Lin J P, Chuang J Y, Chang W C, Wu J Y, Tyan Y S, 2005. *Berberine inhibits arylamine N-acetyltransferase activity and gene expression in mouse leukemia L 1210 cells*. Phytomedicine. May; 12(5):351-8.

Lin J P, Yang J S, Lee J H, Hsieh W T, Chung J G. 2006. *Berberine induces cell cycle arrest and apoptosis in human gastric carcinoma SNU-5 cell line*. World J Gastroenterol. January 7; 12(1):21-8

Lin C C, Kao S T, Chen G W, Ho H C, Chung J G, 2006a. *Apoptosis of human leukemia HL-60 cells and murine leukemia WEHI-3 cells induced by berberine through the activation of caspase-3*. Anticancer Res. January-February; 26(1A):227-42.

Lin C C, Lin S Y, Chung J G, Lin J P, Chen G W, Kao S T, 2006b. *Down-regulation of cyclin B1 and up-regulation of Wee1 by berberine promotes entry of leukemia cells into the G2/M-phase of the cell cycle*. Anticancer Res. March-April; 26(2A):1097-104.

Lin S, Tsai S C, Lee C C, Wang B W, Liou J Y, Shyu K G, 2004. *Berberine inhibits HIF-1 alpha expression via enhanced proteolysis* Mol. Pharmacol. September; 66(3): 612-9.

Mahady G B, Pendland S L, Stoia A, Chadwick L R., 2003. *In vitro susceptibility of Helicobacter pylori to isoquinoline alkaloids from Sanguinaria canadensis and Hydrastis canadensis*. Phytother Res. March; 17(3):217-21.

Mann, C. M., Cox, S. D. and J. L. Markham. 2000. *The outer membrane of Pseudomonas aeruginosa NCTC 6749 confers tolerance to the essential oil of Melaleuca alternifolia (tea tree oil)*. Letters in Appl. Microbiol 30:294-297.

Mantena S K, Sharma S D, Katiyar S K, 2006a. *Berberine, a natural product, induces G1-phase cell cycle arrest and caspase-3-dependent apoptosis in human prostate carcinoma Cells*. Mol Cancer Ther. February; 5(2):296-308.

Mantena S K, Sharma S D, Katiyar S K, 2006b. *Berberine inhibits growth, induces G1 arrest and apoptosis in human epidermoid carcinoma A431 cells by regulating Cdki-Cdk-cyclin cascade, disruption of mitochondrial membrane potential and cleavage of caspase 3 and PARP*. Carcinogenesis. October; 27(10):2018-27.

Musumeci R, Speciale A, Costanzo R, Annino A, Ragusa S, Rapisarda A, Pappalardo M S, Iauk L., 2003. *Berberis aetnensis C. Presl. extracts: antimicrobial properties and interaction with ciprofloxacin*. Int J Antimicrob Agents. July; 22(1):48-53.

Maron, D. M., Ames, B. N., 1983. Revised methods for the *Salmonella* mutagenicity test. Mutat. Res. 113, 173-215

Midwest Research Institute (MRI), 2001. *Analysis of Goldenseal Root Powder From Plantation Medicinals, Lot No. 007-090200*. NIEHS Contract # N01-ES-05457. 425 Volker Blvd., Kansas City, Mo. 64110.

NCCLS Document M26-A, *Methods for Determining Bactericidal Activity of Antimicrobial Agents*, Vol. 19 No. 18.

National Toxicology Program (NTP), 1997. *Goldenseal (Hydrastis canadensis L.) and Two of Its Constituent Alkaloids, Berberine and Hydrastine*. Review of Toxicological Literature. Prepared for The National Toxicology Program by Integrated Laboratory Systems, Research Triangle Park, N.C. 27709.

National Toxicology Program (NTP), 2003. *Final Study Report: Developmental Toxicity Evaluation for Goldenseal (Hydrastis canadensis) Root Powder Administered in the Feed to Swiss (CD-1 7) Mice on Gestional Days 6-17*. Accessed on the world wide web at http://ntp-server.niehs.nih.pgov/htdocs/TTstudies/TER99004.html NIH, 2000. NIH Guide: Botanical Products Development: SBIR and STTR. http://grants2.nih.gov/grants/guide/rfa-files/RFA-AT-00-003.html.

Norio Iizuka, Koji Miyamotoa, Kiwamu Okitac, Akira Tangokub, Hiroto Hayashib, Shigehumi Yosinob, Toshihiro Abeb, Takayuki Moriokab, Shoichi Hazamab, Masaaki Okab, 2000. *Inhibitory effect of Coptidis Rhizoma and berberine on the proliferation of human esophageal cancer cell lines*. Cancer Letters 148 (2000) 19-25.

Oh K B, Oh M N, Kim J G, Shin D S, Shin J, 2006. *Inhibition of sortase-mediated Staphylococcus aureus adhesion to fibronectin via fibronectin-binding protein by sortase Inhibitors*. Appl Microbiol Biotechnol. March; 70(1):102-6.

Ovadekova R, Jantova S, Letasiova S, Stepanek I, Labuda J, 2006. *Nanostructured electrochemical DNA biosensors for detection of the effect of berberine on DNA from cancer cells*. Anal Bioanal Chem. December; 386(7-8):2055-62.

Pan G Y, Wang G J, Sun J G, Huang Z J, Zhao X C, Gu Y, Lin X D, 2003. *Inhibitory action of berberine on glucose absorption*. Yao Xue Xue Bao Pan G Y, Huang Z J, Wang G J, Fawcett J P, Liu X D, Zhao X C, Sun J G, Xie Y Y, 2003. *The antihyperglycaemic activity of berberine arises from a decrease of glucose Absorption*. Planta Med. July; 69(7):632-6.

Pan G Y, Wang G J, Liu X D, Fawcett J P, Xie Y Y, 2002. *The involvement of P-glycoprotein in berberine absorption*. Pharmacol Toxicol. October; 91(4):193-7.

Pan L R, Tang Q, Fu Q, Hu B R, Xiang J Z, Qian J Q, 2005. *Roles of nitric oxide in protective effect of berberine in ethanol-induced gastric ulcer mice*. Acta Pharmacol Sin. 2005 November; 26(11):1334-8

Peng P L, Hsieh Y S, Wang C J, Hsu J L, Chou F P, 2006. *Inhibitory effect of berberine on the invasion of human lung cancer cells via decreased productions of urokinase-plasminogen activator and matrix metalloproteinase-2*. Toxicol Appl Pharmacol. July 1; 214(1):8-15.

Rabbani G H, Butler T, Knight J, Sanyal S C, Alam K, 1987. *Randomized controlled trial of berberine sulfate therapy for diarrhea due to enterotoxigenic Escherichia coli and Vibrio cholerae*. J. Infect. Dis. May; 155(5):979-84.

Pearson, R. D., R. T. Steigbigel, H. T. Davis, and S. W. Chapman. 1980. *Method for reliable determination of minimal lethal antibiotic concentrations*. Antimicrob. Agents Chemother. 23: 142-150

Reed, L. J. and H. A. Muench. 1938. *A simple method of estimating fifty percent Endpoints*. Am. J. Hyg. 27:493-497.

Ribnicky D. M., Poulev A., O=Neal J., Wnorowski G., Malek D. E., Jager Ralf., Raskin I. 2004. *Toxicological evaluation of the ethanolic extract of Artemisia dracunculus L. for use as a dietary supplement and in functional foods*. Food and Chemical Toxicology 42: 585-598.

Rojas, A., Hernandez, L., Peredai-Miranda, R. and R. Mata. 1992. *Screening for antimicrobial activity of crude drug extracts and pure natural products from Mexican medicinal plants*. J. Ethnopharmacol. 35:275-283.

Sack Bradley R., Jean L. Froehlich, 1982. *Berberine Inhibits Intestinal Secretory Response of Vibrio cholerae and Escherichia coli Enterotoxins*. Infec. And Immun, February 1982, p. 471-475

Sanchez J L, Gelnett J, Petruccelli B, Defraites R F, Taylor D N, 1998. *Diarrheal Disease Incidence and Morbidity Among United States Military Personnel During Short-Term Missions Overseas*. Am. J. Trop. Med. Hyg. 58(3), pp. 299B304

Sandhu R, Prescilla R, Simonelli T M, Edwards D J, 2003. *Influence of goldenseal root on the pharmacokinetics of indinavir*. J Clin Pharmacol. November; 43(11):1283-8.

Scazzocchio, F., M. F. Cometa, L. Tomassini, and M. Palmery, 2001. *Antibacterial Activity of Hydrastis canadensis Extract and its Major Alkaloids*, Planta Medica 67, 561-564.

Shirwaikar A, Shirwaikar A, Rajendran K, Punitha I S, 2006. *In vitro antioxidant studies on the benzyl tetra isoquinoline alkaloid berberine*. Biol Pharm Bull. September; 29(9):1906-10.

Stermitz Frank R., Peter Lorenz, Jeanne N. Tawara, Lauren A. Zenewicz, and Kim Lewis, 2000. *Synergy in a medicinal plant: Antimicrobial action of berberine potentiated by 5=-methoxyhydnocarpin, a multidrug pump inhibitor*. Proc. Natl. Acad. Sci. USA 97 (4): 1433-1437.

Strategic Information and Services (SIS), 2001. *The Market for Herbs and Essential Oils*. Alberta Agriculture, Food and Rural Development. Viewed Mar. 22, 2002 on the World Wide Web at http://www.agric.gov.ab.ca/economic/herbsarticle.html.

Sawsan E l-Masry, M. A. Kornay, and A. H. A. Abou-Donia, 1980. *Colorimetric and Spectrophotometric Determinations of Hydrastis Alkaloids in Pharmaceutical Preparations*. Journal of Pharmaceutical Sciences, 69:5:597-598

Tegos George, Frank R. Stermitz, Olga Lomovskaya, and Kim Lewis 2002. *Multidrug Pump Inhibitors Uncover Remarkable Activity of Plant Antimicrobials*. Antimicrob. Agents Chemother. 46 (10): 3133-3141

Tai Y-H, Fesler J F, Marnane W G, Desjeux J-F 1981. *Antisecretory effects of berberine in rat ileum*. Amer. J. Physiol. 241:G253-G258

Tang L Q, Wei W, Chen L M, Liu S, 2006. *Effects of berberine on diabetes induced by alloxan and a high-fat/high-cholesterol diet in rats*. J. Ethnopharmacol. November 3; 108 (1):109-15.

Tsai P L, Tsai T H, 2004. *Hepatobiliary excretion of berberine*. Drug Metab Dispos. April; 32(4):405-12.

Unified Herbal, 2003, US Executive Summary, http://unified-herbal.com/Marketresearch/cfms/us_es.cfm University of Maryland Medicine (UMM), 2004. Alternative/Complementary Medicine, Goldenseal Fact Sheet. Accessed on the World Wide Web Jul. 31, 2005.

U.S. Army, 2004. Debriefing for SBIR Application A043-183-0761 *Berberine Containing Plants as Natural Broad-Spectrum Prophylaxis for Infectious Diarrhea in Deployed Military Forces and Civilian Populations*.

USFWS, 1997. Amendment to Appendix II of Convention on International Trade in Endangered Species of Wild Fauna and Flora. Proposal to include *Hydrastis canadensis* in Appendix II in Accordance with Article 2, Paragraph 2A. U.S. Fish and Wildlife Service, Washington, D.C.

Vrzal R, Zdarilova A, Ulrichova J, Blaha L, Giesy J P, Dvorak Z., 2005. *Activation of the aryl hydrocarbon receptor by berberine in HepG2 and H4IIE cells: Biphasic effect on CYP1A1*. Biochem Pharmacol. September 15; 70(6):925-36.

Wang F, Zhou H Y, Zhao G, Fu L Y, Cheng L, Chen J G, Yao W X, 2004. *Inhibitory effects of berberine on ion channels of rat hepatocytes*. World J Gastroenterol. October 1; 10(19):2842-5.

Wang F, Zhao G, Cheng L, Zhou H Y, Fu L Y, Yao W X, 2004. *Effects of berberine on potassium currents in acutely isolated CA1 pyramidal neurons of rat hippocampus*. Brain Res. February 27; 999(1):91-7.

Weber, Holly A.; Zart, Matthew K.; Hodges, Andrew E.; Molloy, H. Michael; O'Brien, Brandon M.; Moody, Leslie A.; Clark, Alice P.; Harris, Roger K.; Overstreet, J. Diane; Smith, Cynthia S. (2003). *Chemical Comparison of Goldenseal (Hydrastis canadensis L.) Root Powder from Three Commercial Suppliers*. Midwest Research Institute, Kansas City, Mo., USA. Journal of Agricultural and Food Chemistry, 51(25),7352-7358.

Wu X, Li Q, Xin H, Yu A, Zhong M, 2005. *Effects of berberine on the blood concentration of cyclosporin A in renal transplanted recipients: clinical and pharmacokinetic study*. Eur J Clin Pharmacol. September; 61(8):567-72.

Yang J, Wang H D, Lu D X, Wang Y P, Qi R B, Li J, Li F, Li C, 2006. *Effects of neutral sulfate berberine on LPS-induced cardiomyocyte TNF-alpha secretion, abnormal calcium cycling, and cardiac dysfunction in rats*. J. Acta Pharmacol Sin. February; 27(2):173-8.

Yao M, Ritchie H E, Brown-Woodman P D, 2005. *A reproductive screening test of Goldenseal*. Birth Defects Res B Dev Reprod Toxicol. 2005 October; 74(5):399-404

Yesilada E, Kupeli, E, 2002. *Berberis crataegina DC. Root exhibits potent anti-inflammatory, analgesic and febrifuge effects in mice and rats*. J Ethnopharmacol. 79 (2):237-248

Yokozawa T, Ishida A, Kashiwada Y, Cho E J, Kim H Y, Ikeshiro Y, 2004. *Coptidis Rhizoma: protective effects against peroxynitrite-induced oxidative damage and elucidation of its active components*. J Pharm Pharmacol. April; 56(4):547-56.

Yount G, Qian Y, Moore D, et al., 2004. *Berberine sensitizes human glioma cells, but not normal glial cells, to ionizing radiation in vitro*. J Exp Ther Oncol. July; 4(2):137-43.

Xin H W, Wu X C, Li Q, Yu A R, Zhong M Y, Liu Y Y, 2006. *The effects of berberine on the pharmacokinetics of cyclosporin A in healthy volunteers.* Methods Find Exp Clin Pharmacol. January-February; 28(1):25-9.

Xu L H, Liu Y, He X H, 2005. *Inhibitory effects of berberine on the activation and cell cycle progression of human peripheral lymphocytes.* Cell Mol. Immunol. August; 2(4): 295-300.

Zeng X H, Zeng X J, Li Y Y. *Efficacy and safety of berberine for congestive heart failure secondary to ischemic or idiopathic dilated cardiomyopathy.* Am J Cardiol. 2003 Jul. 15; 92(2):173-6.

Zhang R X, Dougherty D V, Rosenblum M L, 1990. *Laboratory studies of berberine used alone and in combination with 1,3-bis(2-chloroethyl)-1-nitrosourea to treat malignant brain tumors.* Chin Med J (Eng) August; 103(8):658-65.

Zhou H, Mineshita S. 2000. *The effect of berberine chloride on experimental colitis in rats in vivo and in vitro.* J Pharmacol Exp Ther. 294(3):822-829.

Zhou L B, Chen M D, Wang X, Song H D, Yang Y, Tang J F, Li F Y, Xu M Y, Chen J L, 2003. *Effect of berberine on the differentiation of adipocyte* Zhonghua Yi Xue Za Zhi. February 25; 83(4):338-40.

Zhu B., Ahrens F. 1983. *Antisecretory effects of berberine with morphine, clonidine, L-phenylephrine, yohimbine or neostigmine in pig jejunum.* Eur. J. Pharmacol. 9; 96(1-2): 11-9

Zhu F, Qian C, 2006. *Berberine chloride can ameliorate the spatial memory impairment and increase the expression of interleukin-1 beta and inducible nitric oxide synthase in the rat model of Alzheimer's disease.* BMC Neurosci. December 1; 7:78.

Zuo F, Nakamura N, Akao T, Hattori M, 2006. *Pharmacokinetics of berberine and its main metabolites in conventional and pseudo germ-free rats determined by liquid chromatography/ion trap mass spectrometry.* Drug Metab Dispos. December; 34(12):2064-72.

I claim:

1. A standardized process of reproducibly extracting the biologically active components from a goldenseal plant or plant part thereof in order to obtain a composition having a desired level of biological activity, the method comprising:
   (a) harvesting goldenseal plants to obtain a combination of reproductive and sterile goldenseal plants;
   (b) separating the reproductive plants and the sterile plants;
   (c) separating the various plant parts from both the separated reproductive plants and the sterile plants;
   (d) performing a plurality of solvent extractions of the separated plant parts using a selected solvent system in a plurality of separate extractions, to produce a plurality of crude extracts;
   (e) sampling each of the plurality of crude extracts of step (d) and analyzing the samples to determine the level of biological activity of each of said samples compared to a reference standard having a known level of biological activity;
   (f) obtaining a specified multiple or fraction of the biological activity of each such extract sample tested as compared to the reference standard; and
   (g) combining those crude extracts from the plurality of extracts from either or both of the extracts obtained from the reproductive plants and/or sterile plants to obtain a composition having the desired level of biological activity as compared to the reference standard; and
   (h) optionally concentrating the combined extract to remove the solvent to provide a composition having the desired level of biological activity.

2. The process of claim 1 wherein the reference standard comprises one or more alkaloid active components.

3. The process of claim 2 wherein the reference standard comprises berberine, hydrastine, or a combination thereof.

4. The process of claim 1 wherein the separated parts are chopped up before the extractions.

5. The process of claim 1 wherein the separated parts are grounded into a powder before the extractions.

* * * * *